US009304102B2

(12) United States Patent
Day et al.

(10) Patent No.: US 9,304,102 B2
(45) Date of Patent: Apr. 5, 2016

(54) AMPEROMETRIC ELECTROCHEMICAL SENSORS, SENSOR SYSTEMS AND DETECTION METHODS

(71) Applicant: NEXTECH MATERIALS, LTD., Lewis Center, OH (US)

(72) Inventors: Michael J. Day, Lake Orion, MI (US); Scott L. Swartz, Columbus, OH (US); Lora B. Thrun, Grove City, OH (US); Buddy E. McCormick, Dublin, OH (US)

(73) Assignee: NexTech Materials, Ltd., Lewis Center, OH (US)

( * ) Notice: Subject to any disclaimer, the term of this patent is extended or adjusted under 35 U.S.C. 154(b) by 452 days.

(21) Appl. No.: 13/791,815

(22) Filed: Mar. 8, 2013

(65) Prior Publication Data

US 2013/0233728 A1  Sep. 12, 2013

Related U.S. Application Data

(60) Provisional application No. 61/608,490, filed on Mar. 8, 2012.

(51) Int. Cl.
*G01N 27/407* (2006.01)
*C04B 35/495* (2006.01)
(Continued)

(52) U.S. Cl.
CPC .......... *G01N 27/4075* (2013.01); *C04B 35/01* (2013.01); *C04B 35/486* (2013.01); *C04B 35/495* (2013.01); *C04B 35/50* (2013.01); *C04B 2235/3206* (2013.01);
(Continued)

(58) Field of Classification Search
CPC .......... G01N 27/4075; G01N 27/409; G01N 33/0037; F01N 2560/00–2560/024
See application file for complete search history.

(56) References Cited

U.S. PATENT DOCUMENTS 3,843,400 A    10/1974  Radford et al.
4,283,261 A    8/1981   Maurer et al.
(Continued)

FOREIGN PATENT DOCUMENTS

DE   19709339      9/1998
WO   9742495       11/1997
WO   2009017485    2/2009

OTHER PUBLICATIONS

Yao et al. "Modification of NASICON Solid Electrolyte for NOx Measurements," Journal of the Electrochemical Society, 151 (4) H75-H80 (2004).*
(Continued)

*Primary Examiner* — Alexander Noguerola
(74) *Attorney, Agent, or Firm* — Porter Wright Morris & Arthur LLP

(57) ABSTRACT

An amperometric electrochemical sensor configured to be operable in an oxidizing atmosphere and under an applied bias to exhibit enhanced reduction of oxygen molecules at the sensing electrode in the presence of one or more target gas species and a resulting measurable increase in oxygen ion flux through the cell. The sensor has an electrolyte membrane, a sensing electrode on the electrolyte membrane, and a counter electrode on the electrolyte membrane, wherein the sensing electrode includes at least one molybdate or tungstate compound. An electrochemical sensor system is also provided, along with a method of detecting the concentration of one or more of NOx and $NH_3$ in a gas sample or stream.

33 Claims, 9 Drawing Sheets

(51) Int. Cl.
*C04B 35/01* (2006.01)
*C04B 35/486* (2006.01)
*C04B 35/50* (2006.01)
*G01N 33/00* (2006.01)

(52) U.S. Cl.
CPC ............ C04B 2235/3208 (2013.01); C04B 2235/3213 (2013.01); C04B 2235/3215 (2013.01); C04B 2235/3224 (2013.01); C04B 2235/3225 (2013.01); C04B 2235/3227 (2013.01); C04B 2235/3229 (2013.01); C04B 2235/3262 (2013.01); C04B 2235/3272 (2013.01); C04B 2235/3275 (2013.01); C04B 2235/3279 (2013.01); C04B 2235/3281 (2013.01); C04B 2235/3284 (2013.01); C04B 2235/3286 (2013.01); C04B 2235/3296 (2013.01); C04B 2235/404 (2013.01); C04B 2235/405 (2013.01); C04B 2235/408 (2013.01); C04B 2235/5409 (2013.01); F01N 2560/026 (2013.01); G01N 33/0037 (2013.01)

(56) References Cited

U.S. PATENT DOCUMENTS

| | | | |
|---|---|---|---|
| 4,770,760 | A | 9/1988 | Noda et al. |
| 5,021,137 | A | 6/1991 | Joshi et al. |
| 5,763,763 | A | 6/1998 | Kato et al. |
| 6,022,464 | A | 2/2000 | Schumann |
| 6,143,165 | A | 11/2000 | Kurosawa et al. |
| 6,312,585 | B1 | 11/2001 | Wahl et al. |
| 6,379,529 | B1 | 4/2002 | Wahl et al. |
| 7,678,329 | B2 | 3/2010 | Montgomery et al. |
| 2001/0008211 | A1 | 7/2001 | Kato et al. |
| 2002/0108871 | A1 | 8/2002 | Wang et al. |
| 2003/0121801 | A1 | 7/2003 | Inaba et al. |
| 2003/0205078 | A1 | 11/2003 | Hasei et al. |
| 2004/0007462 | A1* | 1/2004 | Hotta et al. ............ 204/429 |
| 2004/0118703 | A1 | 6/2004 | Wang et al. |
| 2006/0091022 | A1 | 5/2006 | Ruud et al. |
| 2007/0193883 | A1 | 8/2007 | Garzon et al. |
| 2008/0149499 | A1 | 6/2008 | Ding et al. |
| 2009/0218220 | A1 | 9/2009 | Matter et al. |
| 2010/0264900 | A1 | 10/2010 | Blackburn et al. |
| 2012/0055789 | A1 | 3/2012 | Swartz et al. |

OTHER PUBLICATIONS

Zhong et al., "Sensing Characteristics of potentiometric NO sensor using NASICON and NiW04 sensing electrode", Sensor Letters, American Scientific Publishers, vol. 9, No. 1, Feb. 1, 2011, pp. 307-310.
Tamaki et al., "Application of metal tungstate-carbonate composite to nitrogen oxides sensor operative at elevated temperature," Sensors and Actuators B Chemical 24-25, Apr. 1, 1995, pp. 396-399.
PCT Search Report and Written Opinion, PCT/US2013/030048, Jun. 18, 2013.
English abstract for DE19709339, Sep. 10, 1998.
Machine translation of DE19709339, Sep. 10, 1998.
Dutta A et al: "Amperometric NOX sensor based on oxygen pumping current by using LaGaO3-based solid electrolyte for monitoring exhaust gas" Sensors and Actuators B, Elsevier Sequoia S.A., Lausanne, CH, vol. 108, No. 1-2, Jul. 22, 2005, pp. 309-313.
Sahibzada M et al: "Pd-promoted La0.6Sr0.4Co0.2Fe0.8O3 cathodes" Solid State Ionics, North Holland Pub. Company. Amsterdam, NL, vol. 113-115, Dec. 1, 1998, pp. 285-290.
Sabolsky E M et al.: "Doped-CeO2 Thin-Film Ceramic Membranes for Small-Scale Oxygen Generation Systems" 2005 AICHE Spring National Meeting, Conference Proceedings, 2005, pp. 281-293.
Fergus et al: "Materials for high temperature electrochemical NOx gas sensors" Sensors and Actuators B, Elsevier Sequoia S.A., Lausanne, CH, vol. 121, No. 2, Feb. 3, 2007, pp. 652-663.
Zhuiykov et al: "Development of zirconia-based potentiometric NOx sensors for automotive and energy industries in the early 21st century: What are the prospects for sensors?" Sensors and Actuators B, Elsevier Sequoia S.A., Lausanne, CH, vol. 121, No. 2, Feb. 3, 2007, pp. 639-651.
Reinhardt et al: "Solid electrolytes for gas sensing at high temperatures, multi electrode setup to analyze gas mixtures" Solid-State Sensors and Actuators, and Eurosensors IX (1995), pp. 799-802.
Reinhardt et al: "Electrode reactions of La0.8Sr0.2MnO3 electrodes on stabilized zirconia with oxygen and the nitrogen oxides NO and NO2" Ionics 1 (1995), pp. 32-39.
Szabo et al: "Correlation of sensing behavior of mixed potential sensors with chemical and electrochemical properties of electrodes" Solid State Ionics 171 (2004), pp. 183-190.

\* cited by examiner

AMPEROMETRIC ELECTROCHEMICAL SENSORS, SENSOR SYSTEMS AND DETECTION METHODS

CROSS REFERENCE TO RELATED APPLICATIONS

This application claims priority to U.S. Provisional Patent Application No. 61/608,490, filed Mar. 8, 2012, titled Amperometric Electrochemical Sensors, the entirety of which is incorporated herein by reference.

BACKGROUND

The increase in worldwide industrialization has generated concern regarding pollution created by combustion processes. Particularly, emissions from vehicles or other distributed sources are of concern. New environmental regulations are driving NOx (a mixture of NO and $NO_2$ of varying ratio) emissions from diesel fueled vehicles to increasingly lower levels, with the most challenging of these being the 2010 EPA Tier 2 diesel tailpipe standards.

To meet these emission regulations, engine manufacturers have been developing new diesel after-treatment technologies, such as selective catalyst reduction (SCR) systems and lean NOx traps (LNT). These technologies often require multiple NOx sensors to monitor performance and satisfy on-board diagnostics requirements for tailpipe emissions. Point of generation abatement technologies also have been developed for NOx along with other pollutants, but these solutions can reduce fuel efficiency if they are applied without closed loop control. Further, some of the proposed solutions themselves can be polluting if improperly controlled (e.g., selective catalytic reduction systems for NOx can release ammonia into the atmosphere). Control of these abatement technologies requires compact, sensitive sensors for NOx and other pollutants which are capable of operating in oxygen-containing exhaust streams such as exhaust streams resulting from lean-burn engine operating conditions.

Electrochemical sensors offer a means of measuring gas constituents in an analyte stream using small, low power devices. A number of electrochemical sensor approaches have been reported in the past. These approaches include potentiometric mixed potential sensors, impedance-based sensors and, amperometric sensors. Most of these approaches employ a ceramic electrolyte material as one component of the device, with electrode materials that provide sensitivity to a gas species of interest. A broad scope of materials has been evaluated as the sensing and reference electrodes in these designs. The electrolyte selection generally has been much narrower, focusing principally on yttrium-stabilized zirconia and, in a minority of examples, NASICON electrolytes.

Many of the NOx sensors proposed to date rely on the potentiometric or amperometric measurement of oxygen partial pressure resulting from the decomposition of $NO_2$ molecules to NO, and NO to $N_2$ and $O_2$ in order to determine NOx concentration. Typically, this requires that the sensor be constructed with reference electrodes and/or reference oxygen pumping circuits in order to separate the NOx concentration from the background oxygen concentration.

Potentiometric (or mixed potential) electrochemical sensor designs rely on the different kinetics of reaction to occur at the sensing and reference electrodes. For the example of NOx detection, two reactions are of interest:

the reduction of $NO_2$ to NO: $NO_2 \rightarrow \frac{1}{2}O_2 + NO$; and/or the reverse reaction of oxidation of NO to $NO_2$: $NO + \frac{1}{2}O_2 \rightarrow NO_2$.

These reactions occur at different rates over different electrode materials. The local liberation or consumption of molecular oxygen changes the oxygen partial pressure at the sensing electrode, and results in a change in the electromotive force (EMF) generated in contrast to the reference electrode. Because the reference electrode compensates for oxygen that may be present in the gas stream, the EMF between the sensing and reference electrodes can be correlated directly with the concentration of NO or $NO_2$ present.

Drawbacks to the mixed potential approach include the interference of other gas species with the sensing and reference electrodes. Reducing gases present in the gas stream, such as hydrocarbons and CO, will interfere with the signal. Another complexity of mixed potential devices is that the catalytic reaction between NO and the sensing electrode consumes oxygen, resulting in a negative relative EMF, while the reduction of $NO_2$ generates a positive EMF through the liberation of $O_2$, thus causing inaccurate measurement of total NOx concentration.

Impedance-based electrochemical sensors have also been proposed for NOx sensing applications. In these devices, an oscillating voltage is applied to the sensing electrodes, and the current generated by the voltage is measured. By tailoring the frequency of the voltage oscillations, the response can be selected to correlate with specific non-ohmic contributions to the device resistance. In this approach, the divergent responses of NO and $NO_2$ in mixed potential mode are not observed. Instead, signals of the same sign and magnitude are observed. However, these devices are in the early stages of development and typically experience interference from both $CO_2$ and $H_2O$, both of which will always be present in exhaust streams. In addition, even under simplified operating conditions, impedance-based sensors generally require more complex signal processing than mixed potential or amperometric sensors.

Amperometric sensors, on the other hand, measure the current resulting from a voltage bias applied between the electrodes of an electrochemical cell. Amperometric devices disclosed in the literature typically rely upon the catalytic decomposition of NOx to provide the detected current under the imposed voltage, as shown by the following equations:

the reduction of $NO_2$ to NO: $NO_2 \rightarrow \frac{1}{2}O_2 + NO$, and/or the reduction of NO to $N_2$ and $O_2$: $NO \rightarrow \frac{1}{2}N_2 + \frac{1}{2}O_2$.

Due to the very low concentrations of NOx anticipated in applications such as diesel engine exhaust, the signals achieved by these devices tend to be extremely low, limiting the resolution, accuracy, and detection threshold of these sensors. For tailpipe emissions monitoring of NOx in diesel vehicles, for example, accurate detection of low ppm concentrations of NOx is desired in order to meet various emissions regulations. Additionally, the low signals generated by these devices often require additional shielding to protect the sensor from electromagnetic interference.

Some amperometric sensor designs for detecting NOx rely upon multiple oxygen ion pumps. In this technology, all of the molecular oxygen in the exhaust gas stream is electrochemically pumped from the exhaust gas sample before the remaining NOx is reduced to $N_2$ and $O_2$ by a catalytic electrode material (typically a Pt/Rh alloy) and the resulting oxygen ionic current measured. These sensors typically are relatively slow, complex and costly, and cannot sense the low NOx concentrations needed by the diesel engine industry. Additionally, they exhibit a strong cross-sensitivity to ammonia, causing erroneous NOx measurements in ammonia-containing gas environments. For monitoring NOx breakthrough in either selective catalytic reduction or lean NOx trap systems, resolution of at least 5 ppm or even 3 ppm is often desired.

While a variety of devices and techniques may exist for accurately detecting NOx or other target gas species, it is believed that no one prior to the inventors has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
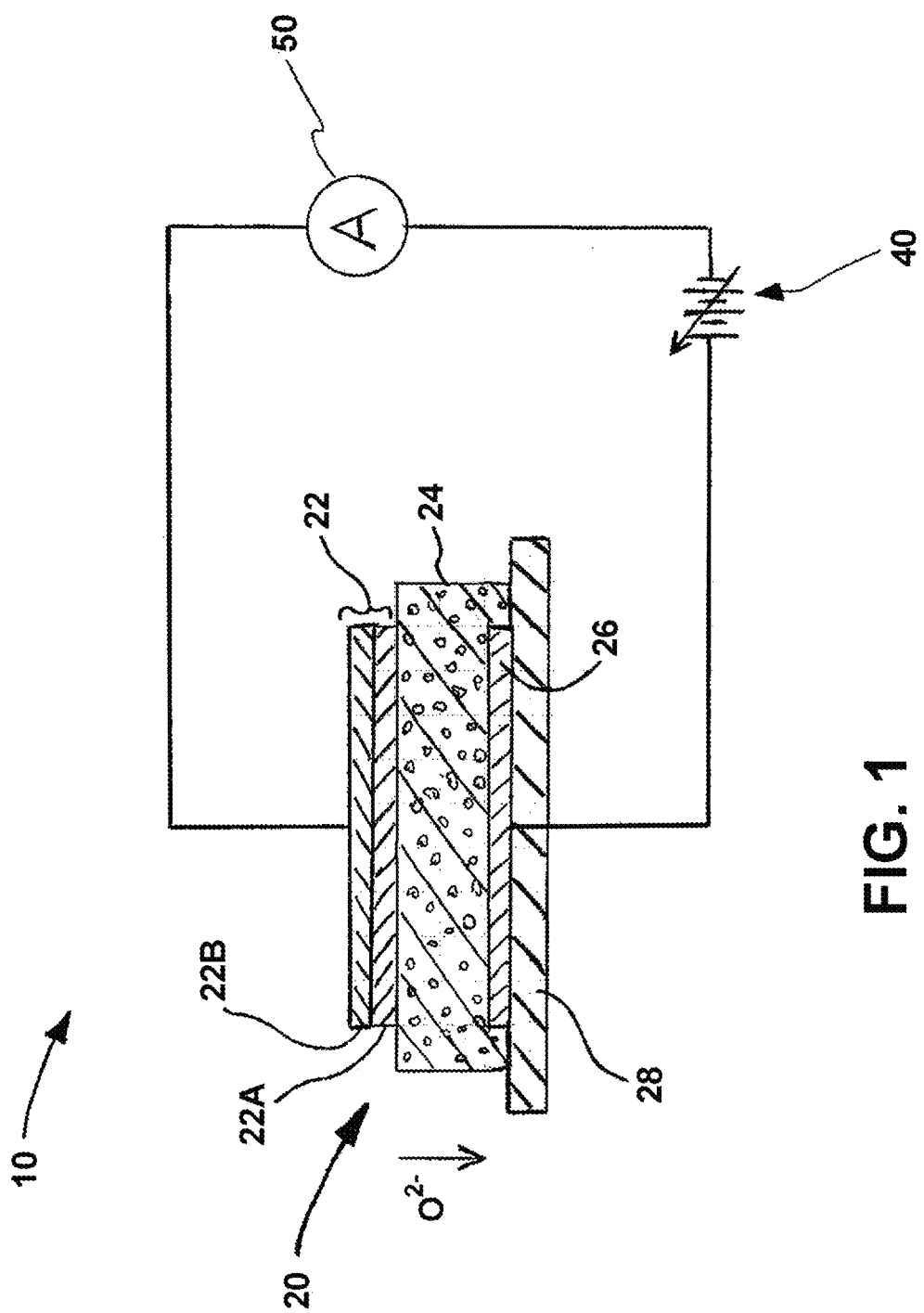
FIG. 1 is a schematic, cross-sectional view of an electrochemical sensor incorporated into a sensor system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

The amperometric electrochemical sensors, sensor systems and detection methods described herein include an electrically conductive sensing electrode comprising at least one molybdate or tungstate compound, and may be used, for example, to detect one more target gas species in a gaseous analyte sample or stream. Applicants have found that by using a molybdate and/or tungstate compound in the sensing electrode, the sensors and sensor systems are robust to $SO_2$ exposure and are highly responsive to NOx levels at desirable temperatures (e.g., 500-600° C.).

By way of example, these amperometric sensors, systems and methods may be used to detect target gas species such as NOx in the oxygen-containing environment of a combusted hydrocarbon fuel exhaust, using, at least in part, an electrocatalytic effect. By way of a more specific example, the amperometric sensors, sensor systems and detection methods can operate in combustion exhaust streams (e.g., from a diesel engine of a vehicle) with significantly enhanced sensitivity to both NOx and ammonia ($NH_3$), with reduced dependence on oxygen partial pressure, providing a fast response even at lower temperatures.

The electrochemical sensors, sensor systems and methods described herein are configured as amperometric devices/methods which respond in a predictable manner when an adsorbed gas species (e.g., NOx) increases the rate of oxygen reduction at the sensing electrode of the device, rather than relying on the decomposition of that gas species (e.g., the catalytic decomposition of NOx) in order to sense target gas (e.g., NOx) concentration. An increase in oxygen reduction current, caused by the presence of adsorbed NOx, is used to detect the presence and/or concentration of NOx in oxygen-containing gas streams. This mechanism is extremely fast and produces a current greater than what is possible from the reduction of NOx alone. Further, this catalytic approach has been demonstrated to extend to $NH_3$.

In some embodiments, the amperometric ceramic electrochemical sensor, comprises: an electrolyte layer comprising a continuous network of a material which is ionically conducting at an operating temperature of about 400 to 700° C.; a counter electrode layer which is electrically conductive at an operating temperature of about 400 to 700° C.; and a sensing electrode layer which is electrically conductive at an operating temperature of about 400 to 700° C., wherein the sensing electrode layer is operable to exhibit increased charge transfer in the presence of one or more target gas species and comprises a molybdate or tungstate compound. The electrolyte layer prevents physical contact between the counter electrode layer and the sensing electrode layer, and the sensor is operable to exhibit conductivity to oxygen ions at an operating temperature of about 400 to 700° C. The sensor is operable to generate an electrical signal as a function of target gas concentration in an oxygen-containing gas stream, in the absence of additional sensing electrodes or oxygen pumping currents. In particular embodiments, the sensing electrode is operable to exhibit varying catalysis of oxygen reduction in the presence of NOx and $NH_3$, even in the presence of variable levels of CO, $CO_2$, and/or SOx. The sensing electrode is operable to exhibit reversible adsorption of NO and $NO_2$.

In some embodiments, the sensor is operable under a first applied bias to exhibit enhanced reduction of oxygen molecules at the sensing electrode in the presence of one or more nitrogen oxides (NOx) and a resulting increase in oxygen ion flux through the cell and is operable in the oxidizing atmosphere and under a second applied bias different from the first applied bias to exhibit enhanced reduction of oxygen molecules at the sensing electrode in the presence of $NH_3$ and a resulting increase in oxygen ion flux through the cell. Alternatively, the sensor may have two or more sensing electrodes and either a common counter electrode or separate counter electrodes for each sensing electrode. The two or more sensing electrodes may thus be operated under different applied biases and/or at different temperatures in order to provide selective detection of two or more target gas species.

As was described in Matter et al. in U.S. Pat. Pub. No. 2009/0218220 A1, published Sep. 3, 2009 and entitled "Amperometric Electrochemical Cells and Sensors" (hereinafter, "Matter et al."), which is incorporated herein by reference, electrode materials such as $(La_{1-x}Sr_x)(Co_{1-y}Fe_y)O_{3-\delta}$ (LSCF) and $(La_{1-x}Sr_x)(Zn_{1-y}Fe_y)O_{3-\delta}$ (LSZF), when applied to an oxygen ion ($O^{2-}$) conducting electrolyte, show enhanced catalytic activity for $O_2$ reduction in the presence of $NO_x$ and/or $NH_3$. As was described by Swartz et al. in U.S. Pat. Pub. No. 2012/0055789 A1, published Mar. 8, 2012 and entitled "Amperometric Electrochemical Cells and Sensors" (hereinafter "Swartz et al."), which is also incorporated herein by reference, other electrode compositions such as a cement mixture of a ceria-based electrolyte material and platinum, also exhibit enhanced catalytic activity for $O_2$ reduction in the presence of NOx and/or $NH_3$. In the present description, the teachings of Matter et al. and Swartz et al. are extended further with the use of sensing electrodes which comprise at least one tungstate and/or molybdate compound.

In Matter et al. and Swartz et al., the sensors described therein detect NOx and $NH_3$ through a catalytic effect in which the reduction of oxygen in a gas stream is catalyzed by the presence of NOx and $NH_3$ species on the surface of the sensing electrode. This feature allows for the manufacture of sensors and sensor systems with advantages such as design simplicity and flexibility, including greater flexibility in materials selection and operating conditions. The sensors of Matter et al. and Swarz et al. also are responsive to NOx in the presence of steam, carbon dioxide and sulfur oxides (SOx), which are additional constituents of diesel exhaust streams.

As further described by Matter et al., the sensors described therein can be made with a tunable response to $NH_3$, which allows only NOx to be detected or both NOx and $NH_3$ to be detected and quantified at the same time. In addition, these sensors can be fabricated to have the ability to detect NO and $NO_2$ at levels as low as 3 ppm and/or to exhibit response times as fast as 50 ms, allowing for better system controls or even engine feedback control. The sensors, sensor systems and detection methods described further herein can be configured to provide these same features, as well as configured to operate in a temperature range of 400 to 700° C. In this temperature range the NOx and $NH_3$ responses are significantly greater than the sensitivity to variable background exhaust gases. In addition, by using the electrically conductive sensing electrodes described herein which comprise at least one molybdate and/or tungstate compound, the sensors and sensor systems are more resistance to sulfur poisoning (particularly $SO_2$ poisoning of the sensor).

While the sensors, sensor systems and detection methods described herein have applicability to the detection of NOx in diesel exhaust systems, including exhaust systems found in heavy duty trucks and stationary generators, the same are also useful in a wide range of other applications in which rapid response to low levels of NOx and/or $NH_3$ is desired. Examples include diesel generator sets, large-scale stationary power generators, turbine engines, natural gas fired boilers and even certain appliances (e.g., natural gas powered furnaces, water heaters, stoves, ovens, etc.). The sensors, sensor systems and detection methods are particularly useful in sensing low levels of NOx in the presence of fixed or variable concentrations of other gases, such as $O_2$, $CO_2$, SOx (SO and/or $SO_2$), $H_2O$, and $NH_3$.

The various electrochemical sensors, sensor systems and detection methods will be described herein by reference to specific electrolyte and electrode compositions, as well as optional catalytic materials, promoters, filter materials, and protective adsorbents. However, the electrochemical sensors, sensor systems and detection methods described herein will yield beneficial results with a wide range of such materials, as further described herein. In addition, while exemplary electrolyte and electrode coating thickness are described, the scope of the present disclosure is not limited to such exemplary coating thicknesses unless the context indicates otherwise. And it will be understood that the thicknesses depicted in the drawings are greatly exaggerated and are not intended to be to scale. Unless the context indicates otherwise, the terms "detect," "detection," and "detecting" are intended to encompass not only the detection of the presence of a target species but also sensing or measuring the amount or concentration of the target species.

FIG. 1 illustrates an exemplary amperometric sensor system (10) comprising an electrochemical sensor (20) as well as circuitry comprising a biasing source (40) and a current measuring device (50) (e.g., an ammeter). Sensor (20) includes a sensing (or working) electrode (22), a counter electrode (26) and an oxygen-ion conducting electrolyte membrane (24) located between the electrodes (22, 26). The electrically conductive sensing electrode (22) comprises at least one molybdate or tungstate compound. A substrate (28) supports counter electrode (26), as shown. Biasing source (40) is configured to apply a voltage bias between the two electrodes (22, 26), and current measuring device (50) is configured to measure the resulting current through sensor (20). Biasing source (40) can comprise any of a variety of power supplies or other devices suitable for applying a bias between the sensing electrode (22) and the counter electrode (26). The applied voltage bias may be regulated by various circuitry and electronic components provided as part of a sensor system, particularly a controller. The controller used for this purpose can have any of a variety of suitable forms and structures known to those skilled in the art. By way of example, the controller can comprise one or more integrated circuits programmed to perform various functions. Such structures are sometimes referred to as microcontrollers, and typically include a processor, programmable memory, and input/output connectors for not only receiving signals (e.g., from the sensor) but also transmitting signals used to drive one or more components (e.g., to control a bias applied between the sensing and counter electrodes). However, the term "controller" is not limited to microcontrollers, and includes one or more microcomputers, PLCs, CPUs, processors, integrated circuits, or any other programmable circuit or combination of circuits.

Likewise, current measuring device (50) may comprise any of a variety of devices and circuits for measuring current such as an op-amp, or other electronic components or structures. For example, the sensor system may be configured to determine the current through the sensor by measuring the voltage across a shunt resistor, in series with the sensor, to determine the current passing through the cell (as shown schematically in FIG. 1)

As further described herein, when sensing electrode (22) is exposed to an oxygen-containing gas and a voltage bias is applied between sensors (22, 26), with sensor (20) heated to an operating temperature, oxygen molecules are reduced at sensing electrode (22). The resulting oxygen ions are conducted through electrolyte membrane (24) to counter electrode (26), whereat the oxygen ions are oxidized to reform $O_2$ and generate a measurable current. In the embodiment shown in FIG. 1, electrolyte membrane (24) is sufficiently porous such that the $O_2$ molecules generated at counter electrode (26) will escape from sensor (20) through porous electrolyte membrane (24). In the embodiment shown, electrolyte membrane (24) extends over the sides of counter electrode (26) such that counter electrode (26) is fully encapsulated between electrolyte membrane (24) and substrate (28). Since the substrate (28) is typically dense (no through porosity which would allow the venting of oxygen gas), oxygen from the counter electrode will be vented through the electrolyte. A dense substrate (28) also will inhibit exhibit poisons from entering the sensor, as well as provide additional strength to the sensor.

In alternative embodiments, one or more gas outlets may be provided in substrate (28) to allow for the escape of $O_2$, with or without the electrolyte membrane (24) being sufficiently porous to allow $O_2$ to escape (i.e., vented) through the electrolyte membrane. For example, one or more gas outlets (e.g., passageways extending through the thickness of substrate (28) may be provided below counter electrode (26) and/or below the portions of electrolyte membrane (24) which are in contact with substrate (28) (when electrolyte membrane (24) is porous).

In still further embodiments, the sensing and counter electrodes may be located on the same surface of the electrolyte membrane, such as described in Matter et al. and Swartz et al. Suitable configurations include, for example, those shown in FIGS. 15 and 17 of Schwartz et al., which do not need gas outlets and the like.

In the sensors, sensor systems and detection methods further described herein, one or more target gas species (e.g., NOx) are reversibly adsorbed by sensing electrode (22) where they catalyze the reduction of $O_2$ at sensing electrode (22). As a result, the concentration of the target gas species in a gas sample or stream can be correlated with the oxygen ion current at any given applied voltage bias and sensor temperature. In this manner, for example, sensor system (10) is operable in an oxidizing atmosphere and under an applied bias to exhibit enhanced reduction of oxygen molecules at sensing electrode (22) in the presence of one or more nitrogen oxides (NOx) and/or ammonia ($NH_3$) and a resulting increase in oxygen ion flux through the sensor (20) (i.e., an increase in the measured current). The counter electrode (26) also can be exposed to the same gas environment as sensing electrode (22), since there is no requirement for an oxygen reference. In one embodiment, sensor (20) is operable to exhibit the enhanced reduction of oxygen molecules at the sensing electrode in the presence of one or more nitrogen oxides and a resulting increase in oxygen ion flux through the sensor in proportion to a concentration of nitrogen oxides in the oxidizing atmosphere.

In another embodiment, an electrochemical sensor for the amperometric detection of one or more gas species is provided. The sensor comprises an ionically conducting electrolyte membrane, a sensing electrode comprising an electrically conducting molybdate and/or tungstate compound, and a counter electrode comprising an electrically conducting ceramic, cement or metal, wherein the electrochemical sensor is operable to pass current by reduction of oxygen at the sensing electrode, transport of oxygen ions through the electrolyte, and recombination of oxygen ions at the counter electrode layer. The sensing electrode is operable to exhibit varying catalysis of oxygen reduction in the presence of NOx (one or more oxides of nitrogen), $NH_3$, CO, $CO_2$, and/or $SO_X$ (one or more oxides of sulfur), or, more specifically, the sensing electrode is operable to exhibit reversible adsorption of NO and $NO_2$ and varying catalysis of oxygen reduction dependent upon the amount of NO and $NO_2$ adsorbed, even in the presence of varying levels of CO, $CO_2$, and/or $SO_X$.

In the examples described herein, the electrically-conductive sensing electrode comprises at least one molybdate or tungstate compound. In some embodiments, the sensing electrode comprises at least one molybdate compound in combination with at least one tungstate compound.

Any of a variety of molybdate and/or tungstate compounds are suitable for use in the sensing electrode such as compounds of the formula $A_X(Mo_{(1-Z)}W_Z)_YO_{(X+3Y)}$, wherein X and Y are each independently selected integers from 1 to 5, $0 \leq Z \leq 1$, and A is one or more ions that form binary compounds with Mo and/or W. By way of more specific example, A is one or more of Mg, Zn, Ni, Co, Fe, Mn, Cu, Ca, Sr, Ba, and Pb. In some embodiments, X and Y are both 1, and Z is 0. Particular examples of such molybdate compounds include: $MgMoO_4$, $ZnMoO_4$, $NiMoO_4$, $CoMoO_4$, $FeMoO_4$, $MnMoO_4$, $CuMoO_4$, $CaMoO_4$, $SrMoO_4$, $BaMoO_4$, and $PbMoO_4$. In other embodiments, X and Y are both 1, and Z is 1. Particular examples of such tungstate compounds include: $MgWO_4$, $ZnWO_4$, $NiWO_4$, $CoWO_4$, $FeWO_4$, $MnWO_4$, $CuWO_4$, $CaWO_4$, $SrWO_4$, $BaWO_4$, and $PbWO_4$.

The sensing electrode comprising at least one molybdate or tungstate compound may have a variety of specific compositions, including, for example:
  (a) a molybdate compound ($A_XMo_YO_{(X+3Y)}$) or a tungstate compound ($A_XW_YO_{(X+3Y)}$), including, for example, a sensing electrode comprising more than 30%, more than 50%, more than 80% or even more than 90% (by volume) of the molybdate or tungstate compound;
  (b) one or more compounds having the formula $A_X(Mo_{(1-Z)}W_Z)_YO_{(X+3Y)}$, wherein X and Y are each independently selected integers from 1 to 5, $0<Z<1$, and A is one or more of Mg, Zn, Ni, Co, Fe, Mn, Cu, Ca, Sr, Ba, and Pb;
  (c) a composite mixture of two or more compounds chosen from the group consisting of molybdate and tungstate compounds, such as a composite mixture of at least one molybdate compound and at least one tungstate compound;

(d) a composite mixture of one or more ceramic electrolyte materials and one or more of (a)-(c);

(e) a composite made from a ceramic phase comprising one or more of (a)-(d), and a metallic phase (e.g., silver, gold, platinum, palladium, rhodium, ruthenium, iridium or alloys or mixtures thereof); or (f) a mixture of two or more of (a)-(e).

In some of the above embodiments, one or more additives or other materials may be added to the sensing electrode composition during fabrication, while in other embodiments no such additives are included.

The above-described molybdate and tungstate compounds, as well as the above-described solid solutions of molybdate and tungstate compounds, may be doped with one or more metals. In addition, or alternatively, one or more oxides may be added, such as manganese oxide, iron oxide, cobalt oxide, vanadium oxide, chromium oxide, tin oxide, niobium oxide, tantalum oxide, ruthenium oxide, indium oxide, titanium oxide, and zirconium oxide. When employed, these oxide additives may be present at an amount of between about 0.1 and 10% by volume in the sensing electrode layer, or between about 1 and 3% by volume in the sensing electrode layer.

As noted above, in some embodiments the sensing electrode comprises a multi-phase composite of: (a) a molybdate and/or tungstate-containing ceramic phase (e.g., a molybdate, a tungstate, a solid solution or composite mixture of a molybdate and a tungstate, or a composite mixture of one or more of the foregoing and an electrolyte); and (b) a metallic phase (Ag, Au, Pt, Pd, Rh, Ru, Ir, or alloys or mixtures thereof). It should be kept in mind that the tungstate/molybdate ceramic phase of such composites may itself comprise more than one phase, such as a composite mixture of one or more molybdate and/or tungstate compounds and an electrolyte.

For the above-described multi-phase ceramic/metal composite materials, the amount of the metallic phase can range from about 0.1% to 10% by weight or about 30 to 70% by volume. At lower levels such as about 0.1% to 10%, or even about 1% to 5%, by weight, the metallic phase is generally present at an amount below the percolation threshold, and therefore does not form a continuous metallic phase which extends through the thickness of the sensing electrode. At higher levels such as about 30% to 70%, or about 40 to 60%, by volume, the metallic phase is generally above the percolation threshold and is therefore present as a continuous phase which extends through the thickness of the sensing electrode (i.e., the composite is a cermet).

In the multi-phase ceramic/metal composites having low levels of the metallic phase (e.g., about 0.1% to 10%, or about 1% to 5% by weight), the metallic phase, particularly Pt, Pd, Rh, Ru, or Ir (or alloys of mixtures thereof), catalyzes the oxidation of NO to $NO_2$ and equilibrates the NO to $NO_2$ ratio in the gas stream. This unexpectedly improves sensitivity to NO and helps provide equal sensitivity to both NO and $NO_2$ (i.e., makes the sensor less susceptible to changes in the NO to $NO_2$ ratio in the exhaust gas). The added metallic phase also promotes NOx and/or $NH_3$ adsorption (i.e., the capacity or rate of NOx or $NH_3$ adsorption), and is believed to selectively enhance oxygen reduction in the presence of NOx.

Higher levels of the metallic phase (e.g., about 30% to 70%, or about 40% to 60% by volume), whether Ag, Au, Pt, Pd, Rh, Ru, or Ir (or alloys or mixtures thereof), on the other hand, improve electrical conductivity (although some sensitivity may be sacrificed). Gold and platinum are particularly useful in this regard.

Figure 2A:
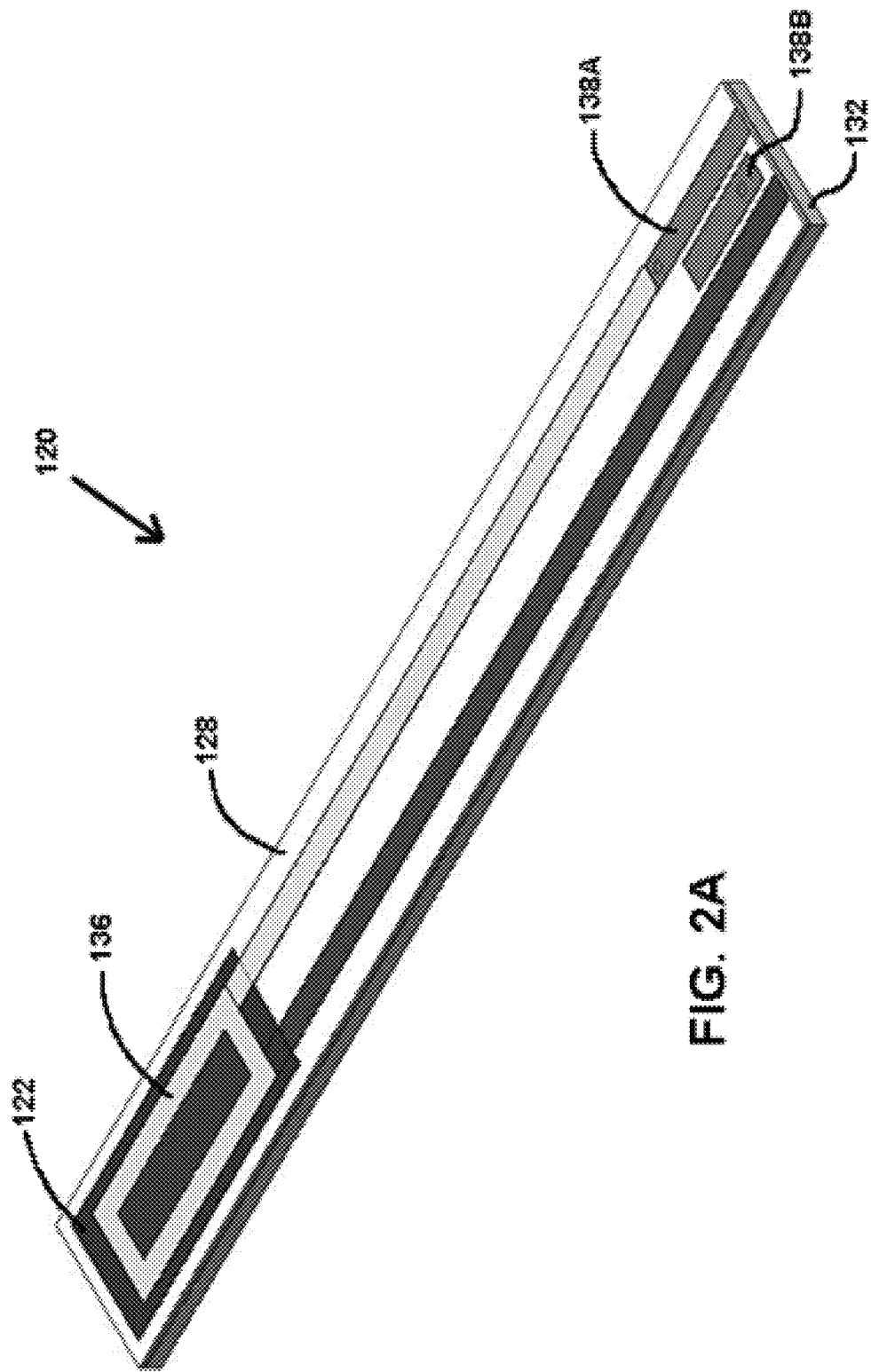
FIGS. 2A and 2B depict, in assembled and exploded views, respectively, a multilayer sensor having electrodes printed on opposite sides of a thick film electrolyte membrane.
Figure 2B:
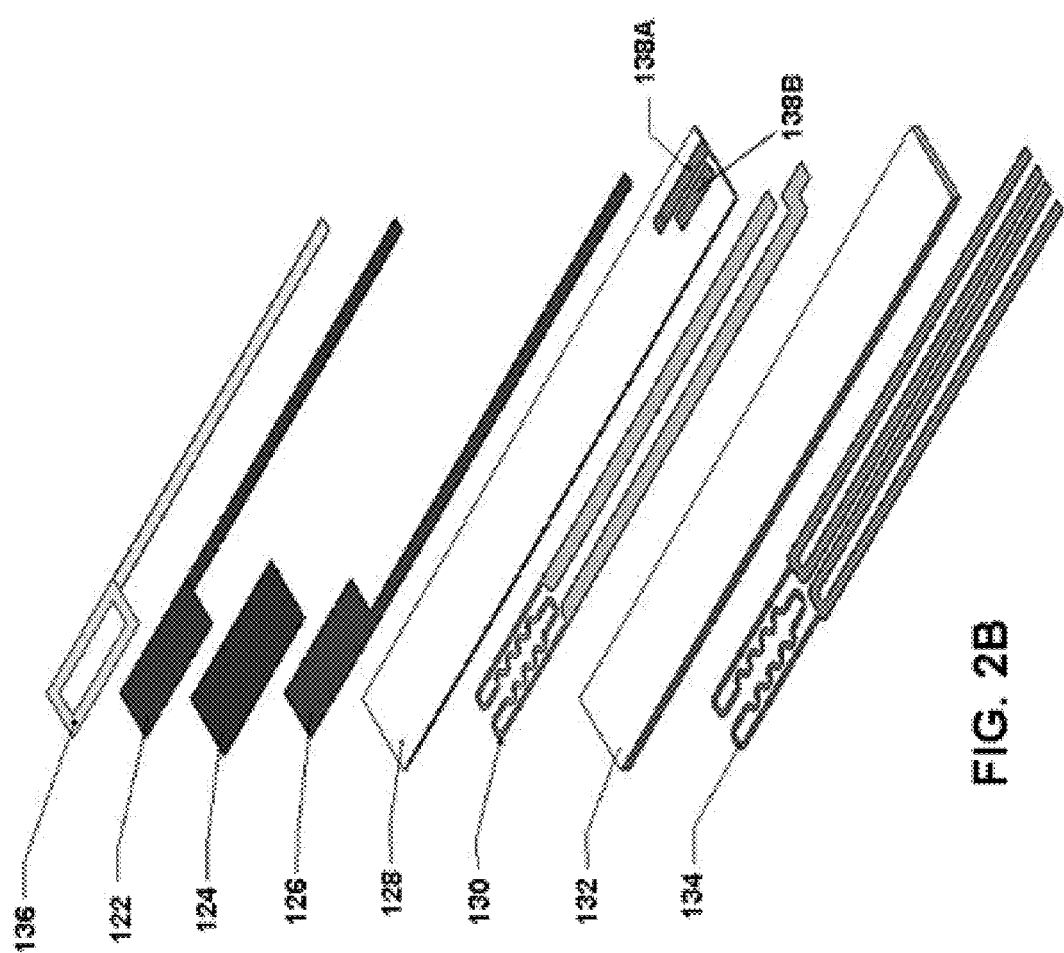

In some embodiments, a multilayer sensing electrode is employed. For example, sensor (20) in FIG. 1 includes a two-layer sensing electrode (22), wherein the layers have different compositions. First layer (22A) is adjacent electrolyte membrane (24), while second layer (22B) is located over first layer (22A). In one embodiment, first and second layers (22A, 22B) each comprise a multi-phase composite: (a) a molybdate and/or tungstate-containing ceramic phase (e.g., a molybdate, a tungstate, a solid solution or composite mixture of a molybdate and a tungstate, or a composite mixture of one or more of the foregoing and an electrolyte such as GDC or SDC); and (b) a metallic phase (Ag, Au, Pt, Pd, Rh, Ru, Ir, or alloys or mixtures thereof). For example, in one embodiment first layer (22A) comprises a multi-phase composite material having about 0.1% to 10%, or even about 2% to 5%, by weight of a metallic phase (e.g., Pt, Pd, Rh, Ru, Ir, or alloys of mixtures thereof) for improved sensitivity. Second layer (22B) comprises a multi-phase composite material having about 30% to 70%, or even about 40% to 60%, by volume of a metallic phase (e.g., Ag, Au, Pt, Pd, Rh, Ru, Ir, or alloys or mixtures thereof) in order to provide improved conductivity. It will be understood that any number of layers may be provided for sensing electrode (22), of varying composition. As an alternative to the embodiment in which second layer (22B) comprises a multi-phase composite having a metallic phase, second layer (22B) may be replaced by a layer of porous metal (e.g., gold or platinum) which thus acts as a current collector (see, e.g., current collector (136) in FIGS. 2A and 2B). When the current collector is configured as shown in FIG. 2B or as a grid, mesh or similar structure, the metal current collector need not be porous, as explained above.

Although first and second layers (22A, 22B) are depicted as being coextensive in FIG. 1 (same footprint such that second layer (22B) completely covers the top surface of first layer (22A)), various other configurations are possible. By way of example, second layer (22B) may be arranged in a grid pattern or as a mesh (e.g., interconnected strands) which provide a plurality of openings such that the gas to be sampled may pass therethrough to first layer (22A). In these arrangements, the material forming second layer (22B) may itself be dense (i.e., non-porous), since the gas to be sampled will pass through the openings in the grid or mesh to reach first layer (22A).

In one specific embodiment, first sensing electrode layer (22A) (the layer in contact with the electrolyte surface) is a composite mixture of a molybdate (or tungstate) phase and a ceria-based electrolyte material, along with a small amount (0.1% to 10%, or even about 1% to 5%) of a metallic material (e.g., Pt, Pd, Rh, Ru, Ir, or alloys of mixtures thereof). Second sensing electrode layer (22B) is a composite mixture of a molybdate (or tungstate) phase, a ceria-based electrolyte material and a larger amount (10% to 70% by volume, or 30% to 70% by volume, or 40% to 60% by volume) of a metallic phase (e.g., Ag, Au, Pt, Pd, Rh, Ru, Ir, or alloys or mixtures thereof). For this embodiment, the second sensing electrode layer (22B) with higher metal content is used to increase the electrical conductivity of the two-layer sensing electrode, facilitating current collection from the device.

For some applications, it is important that the electrode materials be formulated to be operable in temperatures as high as 800 to 1000° C. without adversely affecting sensor performance, as such temperatures can be reached, for example, in certain combustion exhaust sensing applications. For this reason alone, simple oxides such as $MoO_3$ are not suitable for use in sensing electrode (22), since $MoO_3$ has a melting temperature of 795° C.

As noted above, in some embodiments the sensing electrode comprises a composite mixture of: (a) one or more ceramic electrolyte materials (e.g., gadolinium-doped ceria, "GDC," or samarium-doped ceria, "SDC"); (b) one or more molybdate and/or tungstate compounds; and, optionally, (c) a metallic phase (e.g., silver, gold, platinum, palladium, rhodium, ruthenium, iridium, or alloys or mixtures thereof). In these embodiments, the ceramic electrolyte material(s) in the sensing electrode (22) may be any of the electrolytes described below for electrolyte membrane (24), or another ceramic electrolyte material which conducts electricity through the conduction of oxygen ions (i.e., ionic conductivity rather than electronic conductivity). By way of example, suitable ceramic electrolytes for use in the sensing electrode include:

(a) cerium oxide doped with one or more of Ca, Sr, Sc, Y, Pr, Nd, Pm, Sm, Eu, Gd, Tb, Dy, Ho, Er, Tm, Yb, or La;
(b) zirconium oxide doped with one or more of Ca, Mg, Sc, Y, or Ce; and
(c) lanthanum gallium oxide doped with one or more of Sr, Mg, Zn, Co, or Fe.

In more specific embodiments, the ceramic electrolyte used in the sensing electrode comprises cerium oxide doped with one or more of Ca, Sr, Sc, Y, Pr, Nd, Pm, Sm, Eu, Gd, Tb, Dy, Ho, Er, Tm, Yb, or La (e.g., GDC or SDC).

The relative amounts of ceramic electrolyte and one or more molybdate/tungstate compounds in the composite mixtures described in the previous paragraph may be varied depending on, among other things, the nature of the application (e.g., the analyte gas stream/sample and surrounding environment), the configuration of the sensor and/or sensor system, the desired sensitivity, the identity of the target gas(es), etc. In some embodiments, the volumetric ratio of ceramic electrolyte(s) to molybdate/tungstate compound(s) in the sensing electrode or in one or more layers of a multilayer sensing electrode is between about 1:9 and 9:1. In other embodiments, this ratio is between about 2.5:7.5 and 7.5:2.5, or even between about 4:6 and 6:4. And in still other embodiments this ratio is about 1:1. It should be pointed out that the foregoing volumetric ratios are based upon the ratio of the total volume of ceramic electrolytes to the total volume of molybdate and tungstate compounds in the sensing electrode layer in question. When the composite mixtures described in the preceding paragraph include a metallic phase, the nature and amount of the metallic phase may be any of the various metals and amounts described previously (including the multilayer sensing electrodes having varying metals and amounts in each layer).

As noted previously, in addition to the sensing electrode, the sensors described herein also include an ionically-conductive electrolyte membrane and an electrically-conductive counter electrode. Suitable materials for the electrolyte membrane include:

(a) cerium oxide doped with one or more of Ca, Sr, Sc, Y, Pr, Nd, Pm, Sm, Eu, Gd, Tb, Dy, Ho, Er, Tm, Yb, or La;
(b) zirconium oxide doped with one or more of Ca, Mg, Sc, Y, or Ce; and
(c) lanthanum gallium oxide doped with one or more of Sr, Mg, Zn, Co, or Fe.

Cerium oxide doped with one or more of Ca, Sr, Sc, Y, Pr, Nd, Pm, Sm, Eu, Gd, Tb, Dy, Ho, Er, Tm, Yb, or La is particularly suitable, as it is more ionically conductive than doped zirconium oxide or doped lanthanum gallium oxide. In some embodiments, the electrolyte membrane comprises GDC or SDC.

The counter electrode may comprise the same composition as the sensing electrode. Alternatively, the counter electrode may have a different composition from that of the sensing electrode, as this may, for example, facilitate co-sintering during fabrication. In addition to the molybdate/tungstate compositions described previously, suitable materials for the counter electrode include, for example:

(a) a metal comprising Ag, Au, Pt, Pd, Rh, Ru, or Ir, or an alloy, mixture or cement of any of the foregoing (e.g., a cement comprising one or more of these metals, particularly Pt, and YSZ or GDC); and
(b) various other conductive materials suitable for sensor fabrication, particularly materials which catalyze the re-oxidation of oxygen ions to molecular oxygen.

One or more fugitive materials such as carbon black or various starches may be added during fabrication of the counter electrode so that during fabrication the fugitive material is burned away leaving pores (and hence great porosity of the counter electrode).

In one specific embodiment of sensor (20), the compositions are as follows:

(a) electrolyte membrane (24) comprises an ionically-conducting ceria based electrolyte (e.g., cerium oxide doped with one or more of Ca, Sr, Sc, Y, Pr, Nd, Pm, Sm, Eu, Gd, Tb, Dy, Ho, Er, Tm, Yb, La);
(b) sensing electrode (22), single or multilayer configuration, wherein each layer comprises:
a two-phase composite mixture of a molybdate compound and a ceria-based electrolyte, wherein the volumetric ratio of electrolyte to molybdate compound is between about 1:9 and 9:1, between about 2.5:7.5 and 7.5:2.5, between about 4:6 and 6:4, or about 1:1;
a two-phase composite mixture of a tungstate compound and a ceria-based electrolyte, wherein the volumetric ratio of electrolyte to tungstate compound is between about 1:9 and 9:1, between about 2.5:7.5 and 7.5:2.5, between about 4:6 and 6:4, or about 1:1; or
a three-phase composite mixture of a (1) molybdate or tungstate compound, (2) a ceria-based electrolyte, and (3) a metal (e.g., platinum, palladium and/or gold), wherein the volumetric ratio of electrolyte to molybdate compound is between about 1:9 and 9:1, between about 2.5:7.5 and 7.5:2.5, between about 4:6 and 6:4, or about 1:1, and the metal comprises about 0.1% to 10% by weight (e.g., Pt and/or Pd), about 2% to 5% by weight (e.g., Pt and/or Pd), about 30% to 70% by volume (e.g., Pt and/or Au), or about 40% to 60% by volume (e.g., Pt and/or Au) (in terms of the entire weight or volume of the sensing electrode layer); and
(c) counter electrode (26) is an electrically conducting material (e.g., a porous metal, including porous metal alloys).

In yet another specific embodiment, the ionically-conducting electrolyte membrane (24) comprises either Sm-doped cerium oxide (SDC) or Gd-doped cerium oxide (GDC); the sensing electrode (22) comprises $MgMoO_4$, a two-phase composite mixture of SDC and $MgMoO_4$, a two-phase composite mixture of GDC and $MgMoO_4$, a three-phase composite mixture of SDC, $MgMoO_4$ and gold, a three-phase composite mixture of SDC, $MgMoO_4$ and platinum, a three-phase composite mixture of GDC, $MgMoO_4$ and gold, or a three-phase composite mixture of GDC, $MgMoO_4$ and platinum; and the counter electrode (26) is platinum, a cement mixture of platinum and aluminum oxide, or a cement mixture of platinum with an oxygen-ion conducting zirconia or ceria based ceramic electrolyte material (e.g., GDC or SDC).

In still other embodiments of the electrochemical sensors described herein, suitable electrolyte materials for the sensor include gadolinium-doped ceria ($Ce_{1-X}Gd_XO_{2-X/2}$, wherein X ranges from approximately 0.05 to 0.40), and samarium-doped ceria ($Ce_{1-X}Sm_XO_{2-X/2}$, where X ranges from approximately 0.05 to 0.40), such as the specific compositions described further herein. Further ceramic electrolyte materials for use in the sensors include yttrium-doped ceria (YDC), cerium oxide doped with other lanthanide elements, and cerium oxide doped with two or more lanthanide or rare earth elements. Still other suitable electrolyte materials for the disclosed sensor include: fully or partially doped zirconium oxide, including but not limited to yttrium stabilized zirconia (YSZ) and scandium doped zirconia (ScSZ); alkaline earth zirconates and cerates; lanthanum gallate based ceramic electrolytes, such as $(La_{1-X}Sr_X)(Ga_{1-Y}M_Y)O_{3-X/2-Y/2}$, wherein X ranges from approximately 0.05 to 0.30 and Y ranges from approximately 0.05 to 0.30; other ceramic materials that conduct electricity predominantly via transport of oxygen ions; mixed conducting ceramic electrolyte materials; proton-conducting electrolyte materials; and mixtures of two or more of the foregoing. In addition, an interfacial layer of GDC, SDC or another suitable electrolyte material may be provided between the electrolyte membrane and one or both electrodes.

In addition to the metals noted previously, other catalytic or electrocatalytic promoters may optionally be included in either or both of the electrodes, particularly the sensing electrode, in order to improve performance. Such additional promoters may be included, for example, at up to 5% by volume or from about 1% to 2% by volume. Such promoters include, but are not limited to, the following or any combination of the following: Ni, Fe, Cu, Sn, V, Co, W, Mo, Zn, Mn, Cr, Nb or other compositions known to catalyze oxidation of hydrocarbons, CO, $NH_3$, carbon, and other reductants that may interfere with sensor response. If the additional promoter is one which catalyzes carbon oxidation, the promoter will also assist in protecting the sensor from fouling. In some embodiments, the additional promoter may comprise cerium or doped cerium oxide, an alkali metal, or an alkaline earth metal. Like the metal additions noted previously, in specific embodiments, the additional promoter may be added to equilibrate the NO to $NO_2$ ratio in the gas stream or to oxidize NO to $NO_2$ (making the sensor less susceptible to changes in the NO to $NO_2$ ratio in the exhaust gas), to promote NOx or $NH_3$ adsorption on the sensing electrode (i.e., the capacity or rate of NOx or $NH_3$ adsorption), to oxidize NO to $NO_2$, or to selectively enhance oxygen reduction in the presence of NOx. The catalytic or electrocatalytic additional promoter may be added to the sensing electrode layer before the sensing electrode layer is applied to the electrolyte layer, it can be added to the electrode layer (via infiltration from a slurry or solution) after deposition onto the electrolyte, or a separate catalyst or electrocatalyst layer may also be added to the surface of the sensing electrode layer.

Additional promoters that may be added to enhance the capacity or rate of NOx adsorption include but are not limited to potassium, barium, sodium, lanthanum, calcium, strontium, magnesium, and lithium or other alkali or alkaline earth metals and any combination of these materials. Promoters may also be added to decrease electrical resistance of the sensor in the absence of NOx, i.e., to reduce oxygen reduction on the sensor electrode in the absence of NOx, thus improving NOx selectivity over the operating range of the sensor (temperature, voltage, etc.). In these embodiments, the additional promoter can be viewed as an inhibitor. Such additional promoters include, but are not limited to, chlorine, fluorine, potassium, barium, sodium, calcium, lanthanum, strontium, magnesium, and lithium or any combination of these materials. Promoters may also be added to enhance selectivity to $SO_x$, $NH_3$, or other gases to tune the sensor to detection of these gases.

Filter materials and/or protective adsorbent materials may be added to protect the sensor from poisons in the exhaust stream including particulate matter, soot, sulfur compounds, silicon compounds, engine oil contaminants such as phosphorous, zinc, and calcium compounds, lead, road salt, and other application contaminants. These protective materials may be added to the electrode or electrolyte material composition, may be infiltrated into the electrode layer, or may be applied as a coating onto the electrode layer. In a specific embodiment, a protective material is printed on the sensor to cover the electrodes. These materials may be porous in structure and include, but are not limited to, zeolite materials, aluminum oxide, electrolyte materials (as listed above), molybdenum oxide, zinc oxide, tungsten oxide or any other materials that provide a physical or chemical filter and/or have an affinity to preferentially adsorb one or more of these contaminants.

For NOx sensing with the above disclosed sensing electrode materials, in one embodiment of a detection method the sensor is operated in the range of about 400 to 700° C., with an electronic controller regulating the bias voltage applied to the sensor. The applied bias is from about 0.01 to 1 volt, or about 0.05 to 0.5 volts, or about 0.1 to 0.4 volts. The operating temperature range, which also may be controlled with a controller (same or different than the controller used for regulating voltage bias), may be modified to achieve improved selectivity to other gases such as ammonia, $SO_2$, $CO_2$ and/or $O_2$.

Additionally, the applied voltage bias may be constant or varying. In one specific embodiment, the sensor is operated with a constant applied bias in the indicated ranges. In another specific embodiment, the sensor is operated with an applied bias that is modified either to a different range or to an alternating polarity mode, whereby the voltage is cycled between a negative applied voltage and positive applied voltage. The frequency of this cycling may also be adjusted to enhance sensitivity, selectivity, and poison resistance of the sensor. The sensor may also be periodically exposed to a different set of operating conditions such as higher temperature and/or applied voltage bias, or a cycled voltage bias to remove and/or prevent poisoning from sulfur, silica, hydrocarbon particulate matter, or other contaminants, as controlled through the sensor system's electronic controller. For example, a sensor can be constructed with two different electrode materials, one that is sensitive to NOx and a second that is sensitive to $NH_3$, and by alternating the polarity and/or magnitude of the applied voltage across the electrodes, both NOx and $NH_3$ can be measured in a single sensor.

In a specific embodiment, an electrochemical sensor comprising an electrolyte layer, a sensing electrode layer, and a counter electrode layer is operable in an oxidizing atmosphere and under a first applied bias and first temperature to exhibit enhanced reduction of oxygen molecules at the sensing electrode in the presence of a first target species (e.g., one or more nitrogen oxides (NOx)) and a resulting increase in oxygen ion flux through the sensor, and is operable in the oxidizing atmosphere and under a second applied bias different from the first applied bias and/or a second temperature different from the first temperature to exhibit enhanced reduction of oxygen molecules at the sensing electrode in the presence of a second target gas species (e.g., one or more different nitrogen oxides (NOx) or $NH_3$) and a resulting increase in oxygen ion flux through the sensor.

In another embodiment, two electrochemical cells are made on the same device with a single counter electrode, a single electrolyte layer, a first sensing electrode layer that is deposited on a portion of the electrolyte layer surface (to define a first electrochemical cell), and a second sensing electrode layer that is deposited on a different portion of the electrolyte layer surface (to define a second electrochemical cell). This device is operable in an oxidizing atmosphere whereby a first applied bias is applied to the first electrochemical cell to exhibit enhanced reduction of oxygen molecules at the first sensing electrode in the presence of one or more nitrogen oxides (NOx) (or other target gas species) and a resulting increase in oxygen ion flux through the first electrochemical cell, and a second applied bias is applied to the second electrochemical cell to exhibit enhanced reduction of oxygen molecules at the second sensing electrode in the presence of $NH_3$ (or some other target gas species) and a resulting increase in oxygen ion flux through the cell. Alternatively, a sensor may include a combination of discrete cells described herein. In a specific embodiment of such, a sensor comprises (a) a first amperometric ceramic electrochemical cell comprising an electrolyte layer, a sensing electrode layer, and a counter electrode layer, wherein the cell is operable in an oxidizing atmosphere and under a first applied bias to exhibit enhanced reduction of oxygen molecules at the sensing electrode in the presence of, for example, one or more nitrogen oxides (NOx) and a resulting increase in oxygen ion flux through the cell and is operable in the oxidizing atmosphere; and (b) a second amperometric ceramic electrochemical cell comprising an electrolyte layer, a sensing electrode layer, and a counter electrode layer, wherein the cell is operable under a second applied bias different from the first applied bias to exhibit enhanced reduction of oxygen molecules at the sensing electrode in the presence of, for example, $NH_3$ and a resulting increase in oxygen ion flux through the cell.

The sensors and sensor systems herein may be configured to be compatible with various application environments, and may include substrates with modifications to provide structural robustness, the addition of one or more heaters to control sensor temperature, and/or the addition of a resistive temperature detector ("RTD"), a thermistor, a thermocouple or other device to measure temperature and provide feedback to the electronic controller for temperature control. In embodiments further described herein, a 4-wire RTD is employed. Modifications may also be made to the electrolyte geometry and overall sensor size and shape, external packaging and shielding to house and protect the sensor, and appropriate leads and wiring to communicate the sensor signal to an external device or application.

As mentioned previously, the electrolyte membrane may be porous to allow oxygen gas to vent from the counter electrode back to the exhaust gas environment. For example, the electrolyte membrane may have about 10 to 70% porosity, about 20 to 60% porosity, or about 30 to 50% porosity). Use of a porous electrolyte has the added advantage of allowing an electrolyte of different thermal expansion coefficient from the substrate material to be sintered onto the substrate with good integrity. Alternatively, the electrolyte can be made dense such that oxygen gas will not be vented through the electrolyte during use. In such an embodiment, a vent path is added under the counter electrode, for example, to allow oxygen to escape from the sensor through the vent path. The sensor technology described herein is also applicable to both planar and tubular geometries. Additionally, multiple electrochemical cells with different electrode formulations may be employed in a single sensor device to enable detection of multiple gas species. Electrodes may be located on the same side or on opposing sides of the electrolyte layer. Additionally, the sensor may comprise multiple electrochemical cells to increase signal levels. Exemplary embodiments include, but are not limited to, electrochemical cells and sensors wherein the electrode layers are symmetrically opposed to one another on each side of the electrolyte layer, whereby oxygen ion current flows through a thickness of the electrolyte; wherein the electrode layers are laterally spaced on a single surface of the electrolyte layer, with an uncoated area of the surface of the electrolyte layer between the electrode layers; wherein the electrode layers are interspaced to form an interdigitated or interlocking design of electrodes of opposite polarity while maintaining a minimal electrode path length therebetween; and/or wherein the electrolyte layer has a hollow tubular configuration, and the electrode layers are applied internally and/or externally to the electrolyte layer. In one configuration, the electrolyte is a porous component and prevents physical contact between the electrode layers.

Embodiments of the sensors described herein include a substrate, in combination with the described electrochemical cells, to provide mechanical support. The substrate may comprise any suitable insulating material, for example, an insulating ceramic material (e.g., aluminum oxide) or a metal or cement material coated with an insulating material. In one embodiment, a sensor includes a zirconia substrate, or more specifically, an yttrium-stabilized zirconia (YSZ) substrate.

The sensor may optionally include a heater which is electrically isolated from the electrolyte and electrodes. In some embodiments, the heater comprises a resistive heater formed, for example, from a conductive metal such as, but not limited to, platinum, silver, or the like. The heater may, for example, be applied to or embedded in the substrate, or applied to the cell through another insulating layer such as aluminum oxide. In still other embodiments, a temperature measurement mechanism is applied to the sensor to measure temperature and feed that back to the electronic controller to enable closed-loop temperature control. The temperature measurement mechanism, for example, is a resistive temperature device made from a conductive metal or metal/ceramic composite with a high temperature coefficient of resistance (e.g., platinum or a platinum based cement).

In a specific embodiment, the electrochemical sensor is made using tape casting and screen printing techniques commonly used during the manufacture of multilayer ceramic capacitors. The first part of this process involves tape casting of aluminum oxide sheets (or tape). In the green state, via holes are cut into the substrate using a laser cutter or punch, providing electrical pathway connections from an embedded heater or other structures to the contact pads on an outer surface of the ceramic element. Platinum (or platinum based material) is screen printed onto one face of a green aluminum oxide tape in patterns that, after sintering, will provide a heater. Also in the green state, a counter electrode (made of any of the compositions described above) is screen printed onto one face of a green aluminum oxide tape in patterns that after sintering will provide a counter electrode. Multiple layers of green aluminum oxide tape then are aligned and stacked such that the screen-printed heater layer is the middle and the counter electrode layer is on the opposite face. The stack of green alumina tapes then is laminated by application of uniaxial pressure at slightly elevated temperature. The via holes are filled with conductive ink, such as platinum, and the stack is sintered at high temperature to consolidate the aluminum oxide substrate. A porous ceria-based electrolyte (GDC or SDC) layer (or other electrolyte material) is then applied onto the counter electrode face of the substrate by screen printing and sintering. Platinum (or platinum based material) is screen printed onto the outer face of the sintered element, in patterns that, after sintering, will provide an RTD to enable a temperature measurement. Alternatively, another suitable material for an RTD may be applied in the green state prior to sintering of the aluminum oxide substrates and co-sintered therewith. A glass layer is applied over the RTD and cured to protect the RTD in the application. Manufacture of the electrochemical cell or sensor is then completed by screen printing of the sensing electrode layer (made of any of the compositions described above) onto the porous electrolyte layer, followed by sintering of the sensing electrode layer to promote adhesion. A gold (or gold based material) may be applied in a pattern that allows exhaust gas exposure to the sensing electrode layer while providing an electrically conducting pathway to the sensor pads. A porous ceramic coating, such as gamma phase aluminum oxide, can additionally be applied over the sensing electrode to protect it in the application and calcined to improve adhesion. It should be noted that multiple electrochemical cells or sensors can be made simultaneously with the above described process by array processing.

Sensor systems are formed, for example, by coupling one or more of the sensors described herein with one or more electronic controllers configured to controllably apply the bias voltage, control temperature (e.g., through pulse width modulation of the input voltage to the heater based on the sensor temperature measurement supplied to the controller). In some embodiments, the controller is configured to provide a conditioned sensor output, such as calibrated or linearized output.

Methods of detecting, sensing and/or monitoring the concentration of one or more target gas species such as NOx and/or $NH_3$ are also provided, employing any of the various sensors and sensor systems described herein. In these methods, a biasing voltage is applied to the sensor cell and the resulting current is measured. The measured current is correlated with the target gas species at a sensor temperature, based on previously compiled sensor data. In general, the measured current increases as the concentration of target gas species in the gas sample or stream increases. By using predetermined sensor response data, at any given sensor operating temperature and applied biasing voltage, target gas species may be determined on the basis of the generated current through the sensor cell.

In some detection/sensing/monitoring methods, such as for NOx sensing in exhaust or other environments, the active area of the sensor is maintained at a temperature of about 400 to 700° C., or 500 to 600° C., and the applied bias is from about 0.01 to 1 volt, or about 0.05 to 0.5 volts, or even with an applied bias of about 0.1 to 0.4 volts. The phrase "active area" refers to the area of the sensor having the electrolyte membrane, sensing electrode and counter electrodes (i.e., the region of the sensor whereat oxygen is reduced and subsequently oxidized so as to generate current).

Various additional features and advantages of the amperometric sensors, sensor systems and methods will become evident from the devices and results obtained as described under the following Examples.

Example 1

Sensor Testing Platform and Testing Configuration

A multilayer ceramic sensor (120) is used for the testing of various sensing electrode formulations and operating conditions. The structure of this sensor (120) is shown in FIGS. 2A and 2B, and includes a sensing electrode (122), an electrolyte membrane (124), a counter electrode (126), and first and second substrates (128, 132). The planar substrates (128, 132) of sensor (120) were made from several layers of green aluminum oxide tape (approximately 100 microns in thickness) that was fabricated by tape casting. Green aluminum oxide tape layers were stacked to create two laminates with thicknesses of 0.5 and 0.8 mm so as to provide first and second substrates (128, 132), respectively. A platinum layer was screen printed onto one face of the thicker laminate (132) to form the internal resistive heater (130). Via holes 0.6 mm in diameter were cut into the thinner laminate (128) (through the entire thickness) to provide electrical pathways to connect the heater to contact pads (138A, 138B) on the outer face of the first substrate (128). Gold and platinum contact pads (138A, 138B) were screen printed onto the first substrate (128). Another platinum layer was screen printed onto the outer face of the first substrate (128) to form the counter electrode (126), in the shape and form shown in FIGS. 2A and 2B. The two laminates (i.e., the first and second substrates) were then stacked together such that the heater (130) was sandwiched between the substrates (128, 132), with the counter electrode exposed outer face of first substrate (128). The stack of green alumina tapes was then laminated by applying pressure at slightly elevated temperature (at or slightly above the softening temperature of the polymeric binders used during tape casting of the alumina layers).

After lamination, the via holes were filled with platinum ink prior to sintering. The multilayer substrate was completed by heating the component to a temperature (1000° C.) where the organic binders were volatilized, and then further heating the component to much higher temperature (1550° C.) so that the planar multilayer substrates sintered to high density.

Next, a GDC electrolyte layer was screen printed onto one end of the counter electrode (126) on the aluminum oxide substrate (128) and the electrolyte layer was sintered at 1400° C. to form a porous GDC electrolyte layer (124). To increase the thickness of the porous GDC electrolyte membrane (122), two additional GDC layers were then screen printed onto the first GDC layer and sintered at 1400° C. each. The thickness of the porous GDC electrolyte membrane was approximately 45 microns. The nominal dimensions of the substrates were 6 mm wide by 50 mm long. In the active area of the sensor, the electrolyte membrane (124) completely covered counter electrode (126) so that the electrolyte membrane (124) prevents the sensing and counter electrodes from shorting together. Of course both the sensing and counter electrodes have long tail portions which extend away from the active area of the sensor as shown.

A platinum/YSZ cement layer was screen printed onto the bottom face of the second sintered aluminum oxide substrate (132) to form the 4-wire RTD (134) in the pattern shown, and the substrate then was sintered again at 950° C. The four end terminals of the RTD located on bottom of the substrate provide contact pads for the RTD. A protective glass layer (not shown) was applied over the RTD (134), while leaving a portion of each of the end terminals of the RTD exposed so as to maintain contact pads for placing the RTD in electrical communication with a controller or other electronic circuitry. The protective glass layer provides protection of the RTD and substrate, and is cured at 950° C. Multiple such multilayer substrate/counter electrode assemblies were produced for subsequent deposition of various sensing electrodes thereon followed by performance testing, as will described in subsequent examples.

As described below, after application of the sensing electrode (122) on electrolyte (124), a current collector (136) is applied over the sensing electrode. The current collector (136) provides electrical communication between the sensing electrode (122) and contact (138A). Contact pad (138A) is also in electrical communication with the ground/negative terminal of heater (130) and acts as a common ground through which the sensing electrode and heater ground are shorted. Contact pad (138B) is in electrical communication with the positive terminal of heater (130). The end tail portion of counter electrode (126) adjacent contact pad (138B) acts as an electrical pad (for the positive sensor signal).

Figure 3:
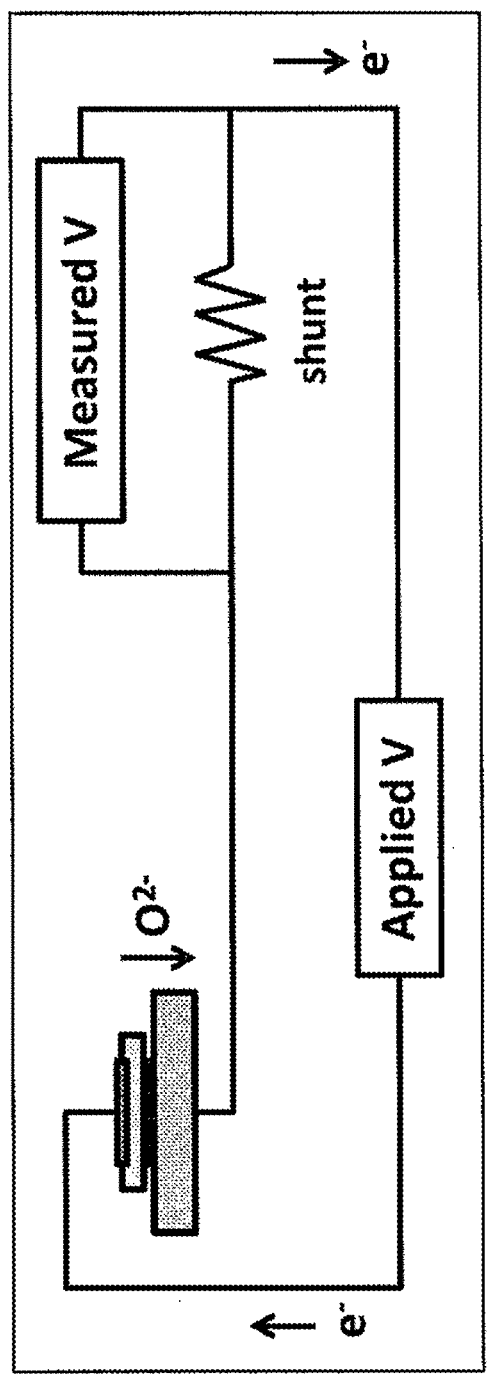
FIG. 3 is a schematic illustration of circuitry for use in conjunction with the sensor of FIG. 2, such as for purposes of testing sensors in the manner described in Example 1 herein.

For testing, the sensor (120) is placed in a simulated fuel-lean diesel exhaust atmosphere, with the sensor temperature being controlled (either with gas temperature being controlled to the test temperature or with the gas temperature being controlled to a temperature less than the test temperature and the internal heater (130) used to maintain the active area of sensor (120) at the test temperature) and a constant biasing voltage in the range of approximately 0.1 to 0.5 volts is applied to the sensor. Voltage is measured across a shunt resistor, in series with the sensor, to determine the current passing through the sensor, with various gases (NOx, $NH_3$, and/or $SO_X$) being introduced into the simulated diesel exhaust atmosphere. The resistance of the shunt resistor is set such that the measured voltage across the shunt resistor in NOx is in the range of 0.1 to 1 mV. The sensor testing configuration is shown in FIG. 3.

Example 2

Fabrication and Testing of Sensor with $MgMoO_4$/GDC Sensing Electrode

This example describes a sensing electrode composition that exhibits responses to nitrogen oxides. A screen printing ink was prepared from a mixture of two powders: 50 volume percent of $MgMoO_4$ having the wolframite crystal structure and with a surface area of 4.1 $m^2$/gram, and 50 volume percent of Gd-doped ceria (GDC) with a surface area of 6.1 $m^2$/gram. The sensing electrode material was screen printed onto the porous GDC electrolyte surface of a multilayer ceramic substrate fabricated as described under Example 1 and then annealed at 1000° C.

Figure 4:
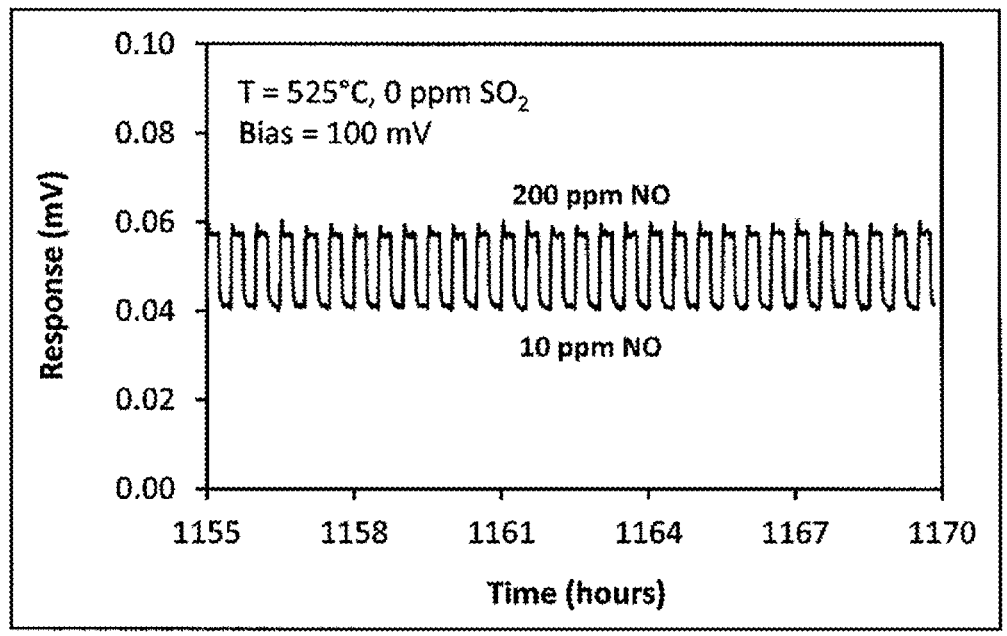
FIG. 4 is a graph depicting the response of an amperometric sensor having a $MgMoO_4$-GDC sensing electrode during cycling between 10 and 200 ppm NO in simulated combustion exhaust (81% $N_2$, 8% $O_2$, 3%, 8% $CO_2$) at 525° C., with 0.1 volts applied across the sensor electrodes, as described in Example 2.
Figure 5:
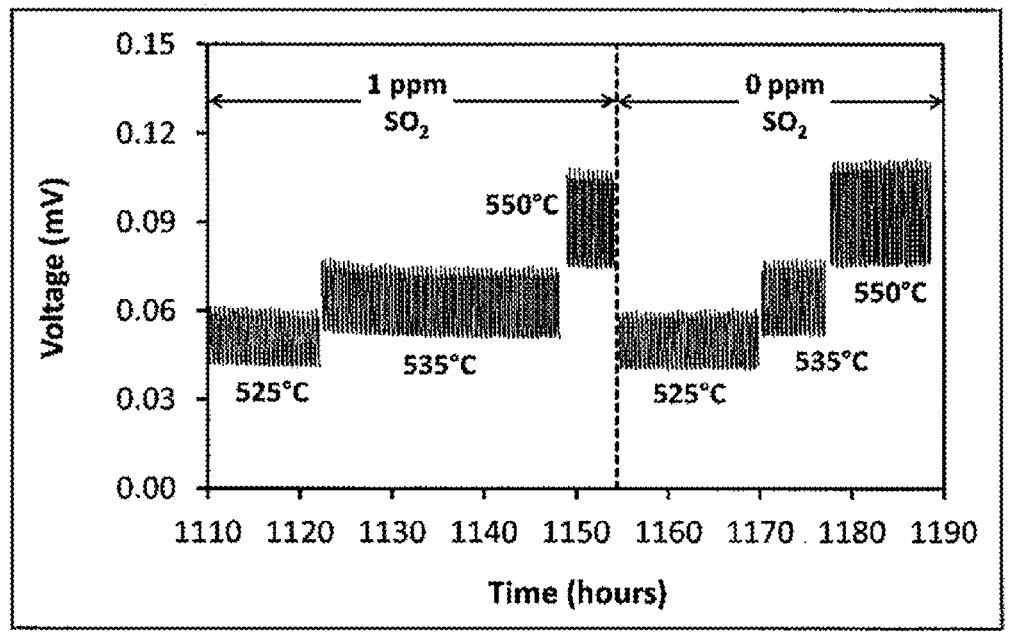
FIG. 5 is a graph depicting the response of an amperometric sensor having a $MgMoO_4$-GDC sensing electrode during cycling between 10 and 200 ppm NO in simulated combustion exhaust (81% $N_2$, 8% $O_2$, 3% $H_2O$, 8% $CO_2$), with and without 1 ppm $SO_2$, at temperatures of 525, 535 and 550° C., with 0.1 volts applied across the sensor electrodes, as described in Example 2.
Figure 6:
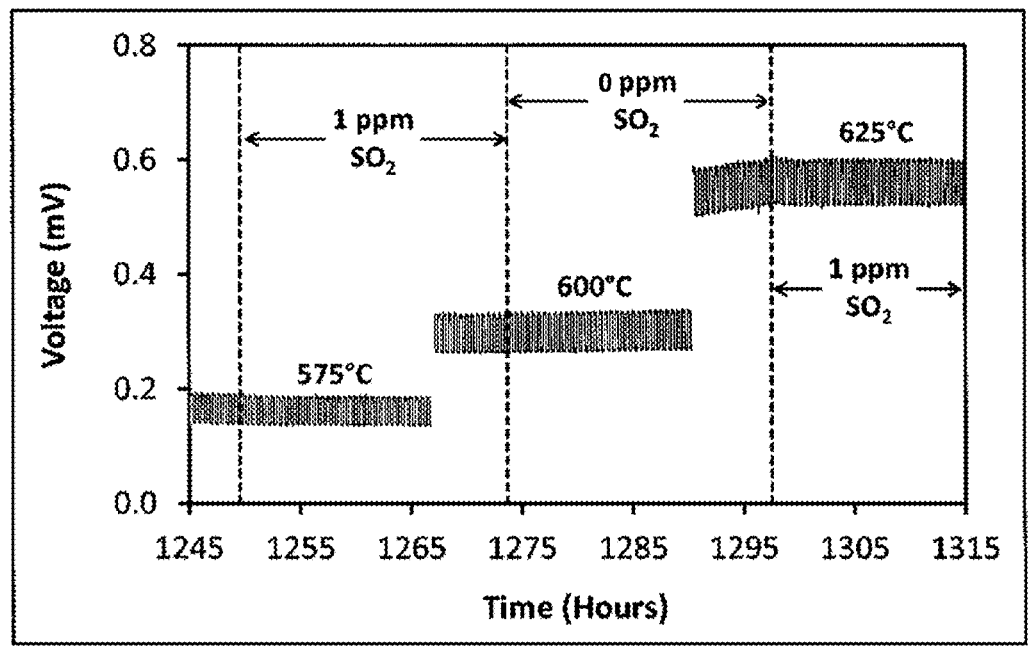
FIG. 6 is a graph depicting the response of an amperometric sensor having a $MgMoO_4$-GDC sensing electrode during cycling between 10 and 200 ppm NO in simulated combustion exhaust (81% $N_2$, 8% $O_2$, 3% $H_2O$, 8% $CO_2$), with and without 1 ppm $SO_2$, at temperatures of 575, 600 and 625° C., with 0.1 volts applied across the sensor electrodes, as described in Example 2.
Figure 7:
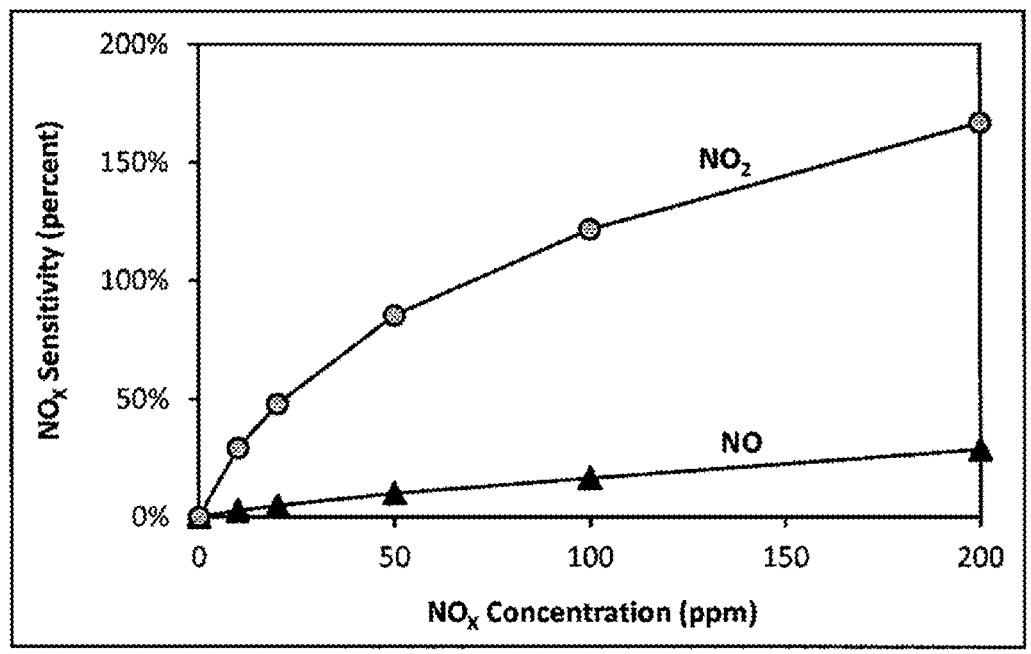
FIG. 7 is a graph depicting the response of an amperometric sensor having a $MgMoO_4$-GDC sensing electrode to different levels of NO and $NO_2$ in simulated combustion exhaust (81% $N_2$, 8% $O_2$, 3% $H_2O$, 8% $CO_2$) containing 1 ppm $SO_2$, at a temperature of 525° C., with 0.1 volts applied across the sensor electrodes, as described in Example 2.

Gold lead wires were attached to the platinum counter electrode and the $MgMoO_4$-GDC sensing electrode. For testing, the sensor was placed in a simulated fuel-lean diesel exhaust atmosphere (81% $N_2$, 8% $O_2$, 3% $H_2O$, 8% $CO_2$), heated to various temperatures (525 to 625° C.) with furnace heat, and a constant potential (bias) of approximately 0.1 volts was applied to the cell. Voltage was measured across a shunt resistor (100 ohms), in series with the sensor, to determine the current passing through the cell. The response of this MMO-GDC sensor composition at 525° C. in the absence of $SO_2$ is shown in FIG. 4, which shows repeatable step changes in sample resistance as the NO concentration is cycled between 10 and 200 ppm. Similar data were obtained at various temperatures between 525 and 625° C., with and without 1 ppm of $SO_2$ in the simulated exhaust background gas (see FIGS. 5 and 6). As shown by these data, the sensor provides stable step-change responses during cycling between 10 and 200 ppm NO throughout the range of 525 to 625° C. Also shown by these data is that there is very little impact of $SO_2$ on the responsiveness of the sensor. In another test of this sensor electrode formulation, the sensitivity to varying levels of NO and $NO_2$ was measured at 525° C. in a simulated fuel-lean diesel exhaust atmosphere (81% $N_2$, 8% $O_2$, 3% $H_2O$, and 8% $CO_2$). These data, presented in FIG. 7, show that the sensitivity to $NO_2$ is substantially higher than the sensitivity to NO.

Example 3

Fabrication and Testing of Sensor with Pt/$MgMoO_4$-GDC Sensing Electrode

Figure 8:
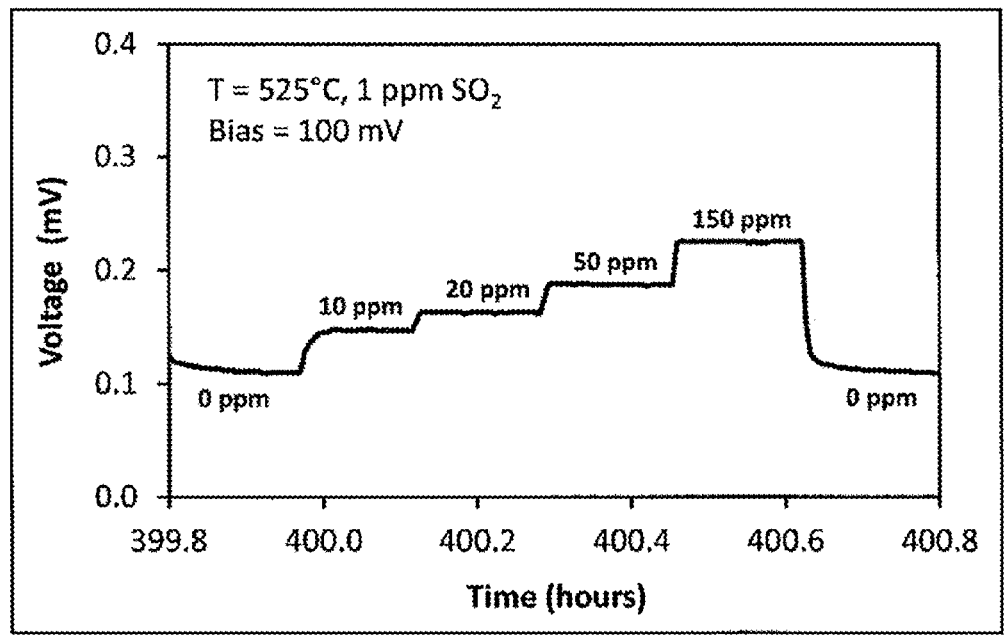
FIG. 8 is a graph depicting the response of an amperometric sensor having a Pt—$MgMoO_4$-GDC sensing electrode during cycling between 0, 10, 20, 50 and 150 ppm NO in simulated combustion exhaust (81% $N_2$, 8% $O_2$, 3% $H_2O$, 8% $CO_2$) containing 1 ppm $SO_2$, at a temperature of 525° C., with 0.1 volts applied across the sensor electrodes, as described in Example 3.
Figure 9:
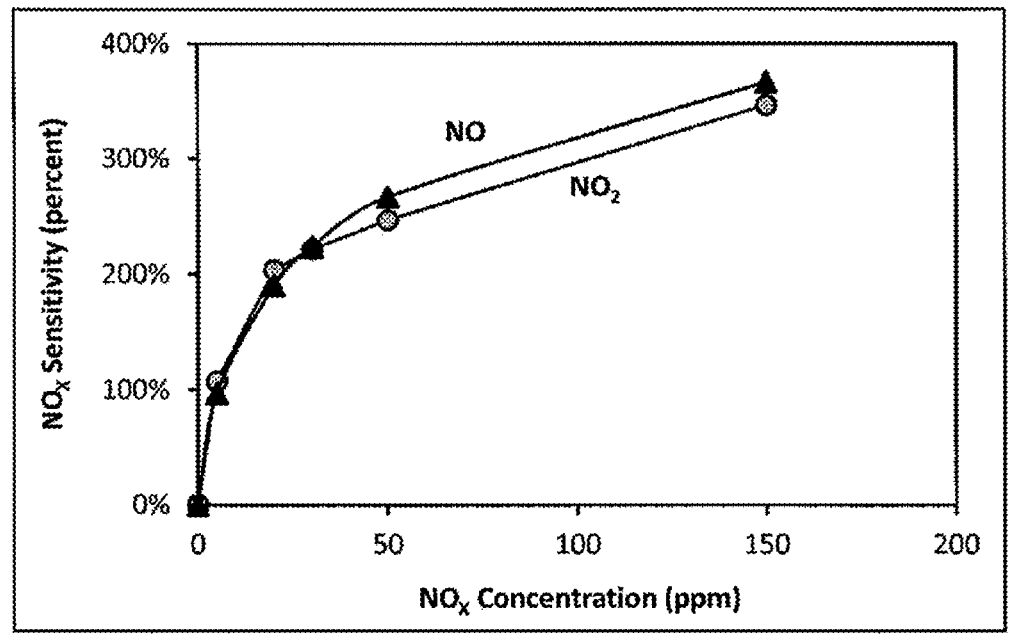
FIG. 9 is a graph depicting the response of an amperometric sensor having a Pt—$MgMoO_4$-GDC sensing electrode to different levels of NO and $NO_2$ in simulated combustion exhaust (80% $N_2$, 8% $O_2$, 8% $CO_2$, 3% $H_2O$, 1 ppm $SO_2$) at a temperature of 525° C., with 0.1 volts applied across the sensor electrodes, as described in Example 3.
Figure 10:
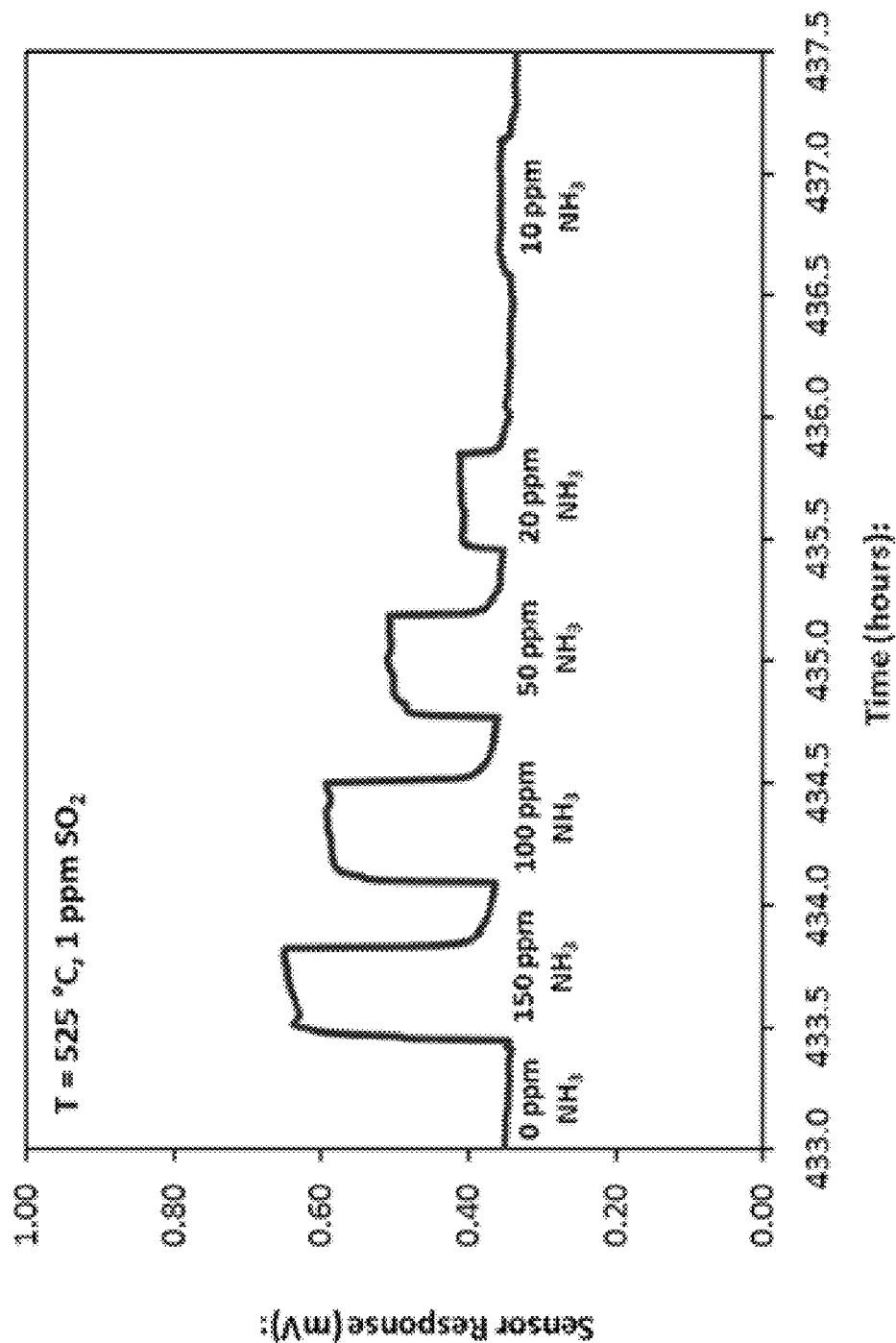
FIG. 10 is a graph depicting the response of an amperometric having a P—$MgMoO_4$-GDC sensing electrode to different levels of $NH_3$ in simulated combustion exhaust (80% $N_2$, 8% $O_2$, 8% $CO_2$, 3% $H_2O$, 1 ppm $SO_2$) at a temperature of 525° C., with 0.1 volts applied across the sensor electrodes, as described in Example 4.

A sensor was prepared in the same configuration and procedure to that described in Example 2, except that the 5 weight percent of platinum powder was added to the composite $MgMoO_4$-GDC mixture prior to screen printing the sensing electrode onto the porous GDC electrolyte coating. Gold lead wires were attached to the platinum counter electrode and the Pt/$MgMoO_4$-GDC sensing electrode. For testing, the sensor was placed in a simulated fuel-lean diesel exhaust atmosphere (81% $N_2$, 8% $O_2$, 3% $H_2O$, 8% $CO_2$), heated to 525° C. with furnace heat, and a constant potential (bias) of approximately 0.1 volts was applied to the cell. Voltage was measured across a shunt resistor (100 ohms), in series with the sensor, to determine the current passing through the cell. The response of this sensor composition at 525° C. in the presence of 1 ppm $SO_2$ is shown in FIG. 8, which shows repeatable step changes in sample resistance as the NO concentration is changed from 0 to 10, 20, 50 and 150 ppm. In another test of this sensor electrode formulation, the sensitivity to varying levels of NO and $NO_2$ was measured at 525° C. in a simulated fuel-lean diesel exhaust atmosphere (81% $N_2$, 8% $O_2$, 3% $H_2O$, and 8% $CO_2$). These data, presented in FIG. 9, show that the sensitivity to $NO_2$ is essentially the same as the sensitivity to NO. It is also evident from these data that the platinum addition to the MMO-GDC sensor formulation had a positive impact in overall sensitivity to NOx compared to the sensor made with the MMO-GDC sensing electrode formulation (without platinum).

Example 4

Testing of Sensor with Pt/$MgMoO_4$-GDC Sensing Electrode for Detecting $NH_3$

A sensor was prepared in the same configuration and procedure to that described in Example 3. For testing, the sensor was placed in a simulated fuel-lean diesel exhaust atmosphere (81% $N_2$, 8% $O_2$, 3% $H_2O$, 8% $CO_2$), heated to 525° C. with furnace heat, and a constant potential (bias) of approximately 0.1 volts was applied to the cell. Voltage was measured across a shunt resistor (100 ohms), in series with the sensor, to determine the current passing through the cell. As shown by FIG. 9, the sensor provides stable step-change responses to $NH_3$.

Example 5

Electrical Circuit Design to be Used in Conjunction with NOx Sensor

Figure 11:
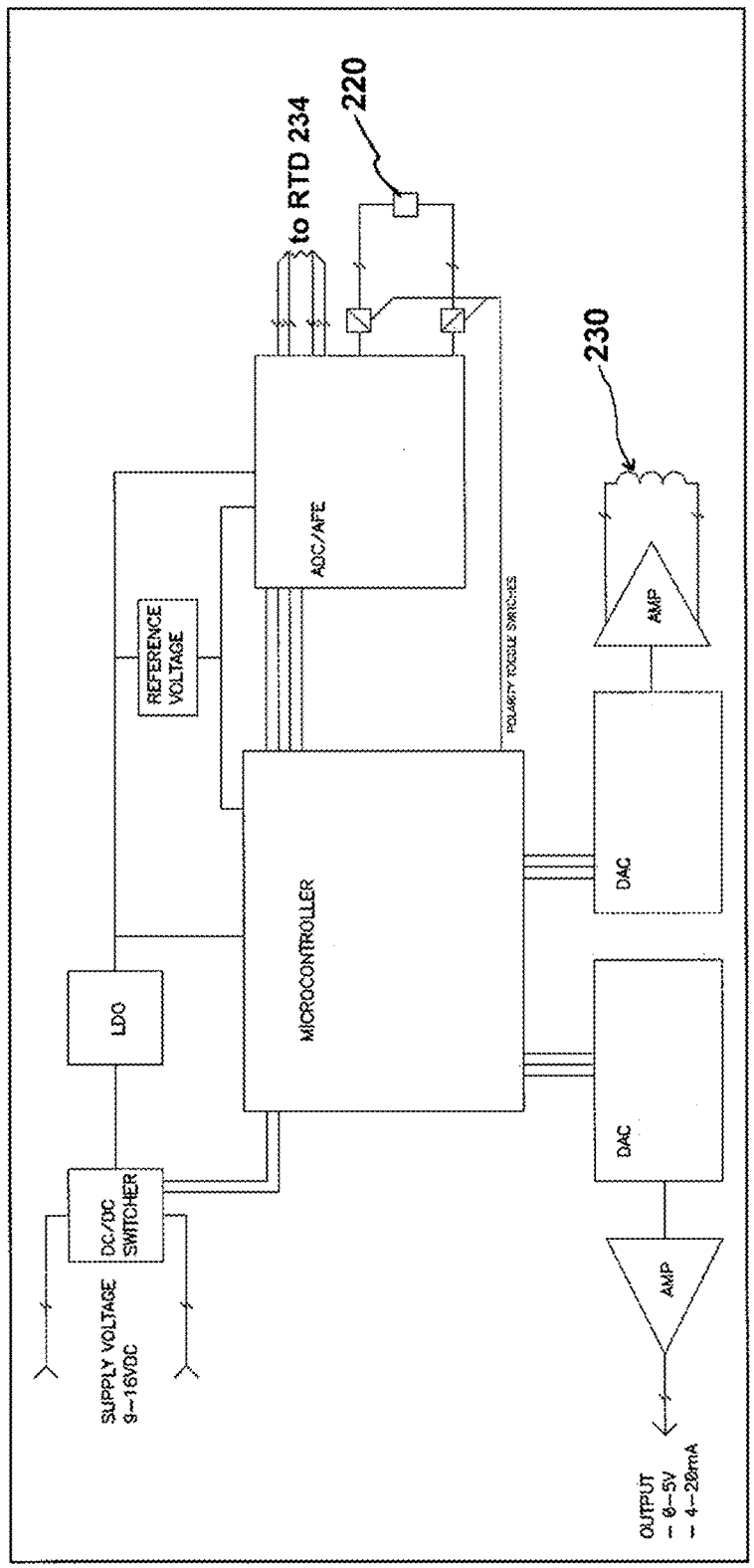
FIG. 11 is a schematic illustration of an alternative embodiment of an amperometric sensor system for use in measuring NOx concentration, as described in Example 5.

The above-described sensors may be connected to an electronic controller, via an electrical wiring harness, in order to form a sensor system. A block diagram of such a sensor system (210) is shown in FIG. 11. Sensor system (210) includes a sensor (220), a heater (230), an RTD (234) (not shown in FIG. 11 apart from the lead wires for the RTD), a microcontroller, a DC power supply, an ADC/AFE board (e.g., a MCP355x available from Microchip Technology, Inc.), various amplifiers and digital-to-analog converters ("DAC"), a DC/DC switcher, a low-dropout regulator, a reference voltage source, and various other switches. The ADC/AFE board is an analog front-end integrated circuit which provides integrated analog-to-digital conversion and signal processing, thus acting as an interface between the sensor (220) and the microcontroller. A wide variety of AFE boards are available for such purpose. The circuitry shown in FIG. 11 includes a microprocessor which provides temperature control (via heater (230)), application of bias voltage, and signal conditioning. For temperature control, the RTD resistance is measured and compared to a pre-defined target that corresponds to the desired sensor operating temperature. The input voltage to the sensor heater is then pulse-width modulated to maintain the RTD at target resistance. The sensor output is measured across a shunt resistor in order to measure current (as a voltage measured across the shunt resistor), and a calibration correction is applied, which is pre-programmed into the microprocessor for each sensor, to report the output as a 0 to 5 V signal indicative of sensor current.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An amperometric electrochemical sensor configured to be operable in an oxidizing atmosphere and under an applied bias for detecting non-oxygen target gas species, the sensor comprising an electrolyte membrane, a sensing electrode on said electrolyte membrane, and a counter electrode on said electrolyte membrane, wherein the sensing electrode comprises at least one molybdate or tungstate compound, wherein said at least one molybdate or tungstate compound comprises $A_X(Mo_{(1-Z)}W_Z)_YO_{(X+3Y)}$, wherein X and Y are each independently selected integers from 1 to 5, $0 \leq Z \leq 1$, and A is one or more of Mg, Zn, Ni, Co, Fe, Mn, Cu, Ca, Sr, Ba, and Pb.

2. The sensor of claim 1, wherein Z is selected from 0 and 1.

3. The sensor of claim 2, wherein X and Y are both 1.

4. The sensor of claim 3, wherein said at least one molybdate or tungstate compound comprises at least one compound chosen from the group consisting of: $MgMoO_4$, $ZnMoO_4$, $NiMoO_4$, $CoMoO_4$, $FeMoO_4$, $MnMoO_4$, $CuMoO_4$, $CaMoO_4$, $SrMoO_4$, $BaMoO_4$, and $PbMoO_4$.

5. The sensor of claim 3, wherein said at least one molybdate or tungstate compound comprises at least one compound chosen from the group consisting of: $MgWO_4$, $ZnWO_4$, $NiWO_4$, $CoWo_4$, $FeWO_4$, $MnWO_4$, $CuWO_4$, $CaWO_4$, $SrWO_4$, $BaWO_4$, and $PbWO_4$.

6. The sensor of claim 1, wherein $0<Z<1$.

7. The sensor of claim 1, wherein said sensing electrode comprises a composite mixture of at least one compound chosen from the group consisting of $A_XMo_YO_{(X+3Y)}$ and at least one compound chosen from the group consisting of $A_XMo_YO_{(X+3Y)}$.

8. The sensor of claim 1, wherein said sensing electrode further comprises either (a) about 0.1% to 10% by weight Pt, Pd, Rh, Ru, Ir, or alloys or mixtures of any of the foregoing metals, or (b) about 30% to 70% by volume of Ag, Au, Pt, Pd, Rh, Ru, Ir, or alloys or mixtures of any of the foregoing metals.

9. The sensor of claim 1, wherein said sensing electrode comprises a composite mixture of: (a) said at least one molybdate or tungstate compound; and (b) at least one ceramic electrolyte material.

10. An amperometric sensor system configured to be operatively connected to a power supply, said sensor system comprising:
    (a) a sensor according to claim 9; and
    (b) a controller configured to apply a voltage bias between the sensing electrode and the counter electrode.

11. The sensor of claim 9, wherein the volumetric ratio of ceramic electrolyte(s) to molybdate/tungstate compound(s) is between about 1:9 and about 9:1.

12. The sensor of claim 11, wherein the volumetric ratio of ceramic electrolyte(s) to molybdate/tungstate compound(s) is between about 4:6 and about 6:4.

13. The sensor of claim 11, wherein said composite mixture further comprises about 0.1% to 10% by weight of: Pt, Pd, Rh, Ru, Ir, or alloys or mixtures of any of the foregoing metals.

14. The sensor of claim 13, wherein said at least one ceramic electrolyte material is chosen from the group consisting of GDC and SDC, and said at least one molybdate or tungstate compound comprises at least one tungstate compound chosen from the group consisting of: $MgWO_4$, $ZnWO_4$, $NiWO_4$, $CoWO_4$, $FeWO_4$, $MnWO_4$, $CuWO_4$, $CaWO_4$, $SrWO_4$, $BaWO_4$, and $PbWO_4$.

15. The sensor of claim 14, wherein said at least one tungstate compound comprises $MgWO_4$ or $CoWO_4$.

16. The sensor of claim 13, wherein said at least one ceramic electrolyte material is chosen from the group consisting of GDC and SDC, and said at least one molybdate or tungstate compound comprises at least one molybdate compound chosen from the group consisting of: $MgMoO_4$, $ZnMoO_4$, $NiMoO_4$, $CoMoO_4$, $FeMoO_4$, $MnMoO_4$, $CuMoO_4$, $CaMoO_4$, $SrMoO_4$, $BaMoO_4$, and $PbMoO_4$.

17. The sensor of claim 16, wherein said at least one molybdate compound comprises $MgMoO_4$ or $CoMoO_4$.

18. The sensor of claim 11, wherein said ceramic electrolyte material is selected from the group consisting of:
    (a) cerium oxide doped with one or more of Ca, Sr, Sc, Y, Pr, Nd, Pm, Sm, Eu, Gd, Tb, Dy, Ho, Er, Tm, Yb, or La;
    (b) zirconium oxide doped with one or more of Ca, Mg, Sc, Y, or Ce; and
    (c) lanthanum gallium oxide doped with one or more of Sr, Mg, Zn, Co, or Fe.

19. The sensor of claim 1, wherein said sensing electrode further comprises about 0.1% to 10% by volume of an oxide chosen from the group consisting of: manganese oxide, iron oxide, cobalt oxide, vanadium oxide, chromium oxide, tin oxide, niobium oxide, tantalum oxide, ruthenium oxide, indium oxide, titanium oxide, zirconium oxide, and mixtures of two or more of the foregoing.

20. The sensor of claim 1, wherein the electrodes are symmetrically opposed to one another on opposite sides of the electrolyte membrane, whereby during use oxygen ion current flows through a thickness of the electrolyte membrane.

21. The sensor of claim 1, wherein the electrolyte membrane is sufficiently porous such that, during use, oxygen is vented from the sensor through the electrolyte membrane.

22. The sensor of claim 1, further comprising a substrate on which said counter electrode is located, the substrate chosen from the group consisting of: an insulating ceramic, a metal coated with an insulating material, and a cermet coated with an insulating material.

23. The sensor of claim 22, further comprising an electrical heater and a temperature measurement device.

24. The sensor of claim 1, wherein the sensing electrode further includes a catalytic or electrocatalytic promoter chosen from the group consisting of: cerium, doped cerium oxide, an alkali metal, an alkaline earth metal, Ag, Au, Pt, Pd, Ru, Ir, Ni, Fe, Cu, Sn, V, Rh, Co, W, Mo, U, Zn, Mn, Cr, Nb and combinations of two or more of the foregoing.

25. The sensor of claim 1, wherein the sensing electrode further includes one or more of Cl, F, K, Ba, Na, Ca, La, Sr, Mg and Li.

26. An amperometric sensor system configured to be operatively connected to a power supply, said sensor system comprising:
  (a) a sensor according to claim 1; and
  (b) a controller configured to apply a voltage bias between the sensing electrode and the counter electrode.

27. A method of detecting one or more target gas species chosen from NOx and $NH_3$ in a gas sample or stream, comprising the steps of:
  (a) locating the active area of a sensor of claim 1 such that the active area is exposed to the gas sample or stream;
  (b) applying a bias to the sensor;
  (c) measuring the resulting current through the sensor; and
  (d) determining the presence and/or concentration of said one or more target gas species based on the measured current.

28. The method of claim 27, wherein the active area of the sensor is maintained at a temperature of about 400 to 700° C., and the applied bias is from about 0.01 to about 1 volt.

29. The method of claim 28, wherein the applied bias is from about 0.05 to about 0.5 volts.

30. An amperometric electrochemical sensor configured to be operable in an oxidizing atmosphere and under an applied bias for detecting non-oxygen target gas species, the sensor comprising an electrolyte membrane, a sensing electrode on said electrolyte membrane, and a counter electrode on said electrolyte membrane, wherein said sensing electrode comprises a composite mixture of:
  (a) a molybdate compound or a tungstate compound;
  (b) a ceramic electrolyte material chosen from the group consisting of GDC and SDC; and
  (c) about 0.1% to 10% by weight of Pt, Pd, Rh, Ru, Ir, or alloys or mixtures of any of the foregoing metals;
wherein the volumetric ratio of the ceramic electrolyte material to the molybdate or tungstate compound is between about 4:6 and about 6:4.

31. An amperometric sensor system configured to be operatively connected to a power supply, said sensor system comprising:
  (a) a sensor according to claim 30; and
  (b) a controller configured to apply a voltage bias between the sensing electrode and the counter electrode.

32. An amperometric electrochemical sensor configured to be operable in an oxidizing atmosphere and under an applied bias for detecting non-oxygen target gas species, the sensor comprising an electrolyte membrane, a sensing electrode on said electrolyte membrane, and a counter electrode on said electrolyte membrane, wherein the sensing electrode comprises first and second layers of different composition, said first layer located on said electrolyte membrane and said second layer located on said first layer,
  wherein said first layer of the sensing electrode comprises a composite mixture of:
    (a) a molybdate or tungstate compound;
    (b) an electrolyte chosen from the group consisting of GDC and SDC; and
    (c) about 0.1% to 10% by weight of Pt, Pd, Rh, Ru, Ir, or alloys or mixtures of any of the foregoing metals;
    wherein the volumetric ratio of the electrolyte to the molybdate compound is between about 1:9 and about 9:1;
  and
  said second layer of the sensing electrode comprises:
    (d) a molybdate or tungstate compound;
    (e) an electrolyte chosen from the group consisting of GDC and SDC; and
    (f) about 30% to 70% by volume of Ag, Au, Pt, Pd, Rh, Ru, Ir, or alloys or mixtures of any of the foregoing metals;
    wherein the volumetric ratio of the electrolyte to the molybdate compound is between about 1:9 and about 9:1.

33. A method of detecting one or more target gas species chosen from NOx and $NH_3$ in a gas sample or stream, comprising the steps of:
  (a) locating the active area of a sensor of claim 30 such that the active area is exposed to the gas sample or stream;
  (b) applying a bias to the sensor;
  (c) measuring the resulting current through the sensor; and
  (d) determining the presence and/or concentration of said one or more target gas species based on the measured current.

* * * * *